(12) United States Patent
Zhang et al.

(10) Patent No.: US 11,342,093 B2
(45) Date of Patent: *May 24, 2022

(54) MULTI-LEAF COLLIMATOR AND DRIVING SYSTEM

(71) Applicant: SHANGHAI UNITED IMAGING HEALTHCARE CO., LTD., Shanghai (CN)

(72) Inventors: Jian Zhang, Shanghai (CN); Xiaolong Liu, Shanghai (CN); Xiao Fang, Shanghai (CN); Hui Zhou, Shanghai (CN); Hui Yin, Shanghai (CN); Xu Chao, Shanghai (CN); Jian Liu, Shanghai (CN)

(73) Assignee: SHANGHAI UNITED IMAGING HEALTHACRE CO., LTD., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/713,678

(22) Filed: Dec. 13, 2019

(65) Prior Publication Data

US 2020/0118701 A1 Apr. 16, 2020

Related U.S. Application Data

(63) Continuation of application No. 15/313,960, filed as application No. PCT/CN2016/098620 on Sep. 9, 2016, now Pat. No. 10,510,456.

(30) Foreign Application Priority Data

Sep. 10, 2015 (CN) .......................... 201520698943.6
Sep. 10, 2015 (CN) .......................... 201520699659.0

(Continued)

(51) Int. Cl.
*G21K 1/04* (2006.01)
*A61B 6/06* (2006.01)
(Continued)

(52) U.S. Cl.
CPC ................ *G21K 1/046* (2013.01); *A61B 6/06* (2013.01); *A61N 5/1045* (2013.01); *G21K 1/04* (2013.01);
(Continued)

(58) Field of Classification Search
CPC ............ G21K 1/00; G21K 1/02; G21K 1/025; G21K 1/04; G21K 1/046; A61B 6/00;
(Continued)

(56) References Cited

U.S. PATENT DOCUMENTS

| 4,143,273 A | 3/1979 | Richey et al. |
| 4,672,212 A | 6/1987 | Brahme |

(Continued)

FOREIGN PATENT DOCUMENTS

| CN | 101058005 A | 10/2007 |
| CN | 201226257 Y | 4/2009 |

(Continued)

OTHER PUBLICATIONS

International Search Report in PCT/CN2016/098620 dated Dec. 2, 2016, 4 pages.

(Continued)

*Primary Examiner* — Anastasia Midkiff
(74) *Attorney, Agent, or Firm* — Metis IP LLC

(57) ABSTRACT

The present disclosure relates to a collimator. The collimator may include a motor, a transmission unit having a first end and a second end, and a leaf unit having a leaf. The first end of the transmission unit may be connected to the motor and the second end of the transmission unit may be connected to the leaf. The present disclosure also relates to a collimator (Continued)

system. The collimator system may include a leaf module having a leaf, a driving module having a motor configured to drive the leaf, and a processing module to generate a movement profile of the leaf. The movement profile of the leaf may include a first speed during a first stage, a second speed of the leaf during a second stage, and a third speed of the leaf during a third stage.

20 Claims, 25 Drawing Sheets

(30) Foreign Application Priority Data

Sep. 14, 2015 (CN) .......................... 201510581866.0
Oct. 12, 2015 (CN) .......................... 201510657060.5

(51) Int. Cl.
*A61N 5/10* (2006.01)
*G21K 1/02* (2006.01)

(52) U.S. Cl.
CPC .......... *G01N 2223/316* (2013.01); *G21K 1/02* (2013.01); *H01J 2237/045* (2013.01); *H01J 2237/0455* (2013.01); *H01J 2237/0456* (2013.01); *H01J 2237/0458* (2013.01)

(58) Field of Classification Search
CPC ... A61B 6/06; A61B 2560/00; A61B 2560/04; A61N 5/1042; A61N 5/1045; A61N 5/1047; A61N 5/1064; A61N 5/1065; A61N 5/1077; H05G 1/00; H05G 1/02; G01N 2223/00; G01N 2223/30; G01N 2223/316; G01N 2223/32; G01N 2223/321; H01J 35/00; H01J 35/02; H01J 35/025; H01J 37/00; H01J 37/02; H01J 37/023; H01J 37/24; H01J 37/243; H01J 2237/00; H01J 2237/02; H01J 2237/024; H01J 2237/04; H01J 2237/045; H01J 2237/0455; H01J 2237/0456; H01J 2237/0458; H01J 2237/06; H01J 2237/061; H01J 2237/083; H01J 2237/0835; H01J 2237/248; H01J 2237/2485; H01J 2237/2487
See application file for complete search history.

(56) References Cited

U.S. PATENT DOCUMENTS

| 4,794,629 | A | 12/1988 | Pastyr et al. |
| 4,868,843 | A | 9/1989 | Nunan |
| 4,987,309 | A | 1/1991 | Klasen et al. |
| 5,889,834 | A | 3/1999 | Vilsmeier et al. |
| 6,188,748 | B1 | 2/2001 | Pastyr et al. |
| 7,020,245 | B2 | 3/2006 | Noguchi |
| 7,642,534 | B2 | 1/2010 | Johnsen |
| 8,335,296 | B2 | 12/2012 | Dehler et al. |
| 10,510,456 | B2 * | 12/2019 | Zhang .................... G21K 1/046 |
| 2006/0067481 | A1 | 3/2006 | Morton |
| 2006/0193441 | A1 | 8/2006 | Cadman |
| 2009/0001295 | A1 | 1/2009 | Johnsen |
| 2009/0262901 | A1 | 10/2009 | Broad et al. |
| 2010/0252754 | A1 | 10/2010 | Brown et al. |
| 2010/0278310 | A1 | 11/2010 | Dehler et al. |
| 2011/0049395 | A1 | 3/2011 | Hashimoto |
| 2012/0004518 | A1 | 1/2012 | D'Souza et al. |
| 2012/0043482 | A1 | 2/2012 | Prince et al. |
| 2012/0203490 | A1 | 8/2012 | Sayeh et al. |
| 2014/0254768 | A1 | 9/2014 | Perkins |

FOREIGN PATENT DOCUMENTS

| CN | 101739034 | A | 6/2010 |
| CN | 201968693 | U | 9/2011 |
| CN | 203634645 | U | 6/2014 |
| CN | 203874296 | U | 10/2014 |
| CN | 203896236 | U | 10/2014 |
| CN | 104240785 | A | 12/2014 |
| CN | 104689490 | A | 6/2015 |
| CN | 104771838 | A | 7/2015 |
| EP | 1712254 | A1 | 10/2006 |
| EP | 2340871 | A2 | 7/2011 |
| JP | 4436343 | B2 | 3/2010 |
| WO | 2017041750 | A1 | 3/2017 |

OTHER PUBLICATIONS

Written Opinion in PCT/CN2016/098620 dated Dec. 2, 2016, 6 pages.
Examination Report in Canadian Application No. 2991083 dated Aug. 30, 2018, 3 pages.
Partial Supplementary European Search Report in European Application No. 16843688.9 dated Mar. 20, 2019, 17 pages.
Office Action in Canadian Application No. 2991083 dated Jul. 17, 2019, 3 pages.

* cited by examiner

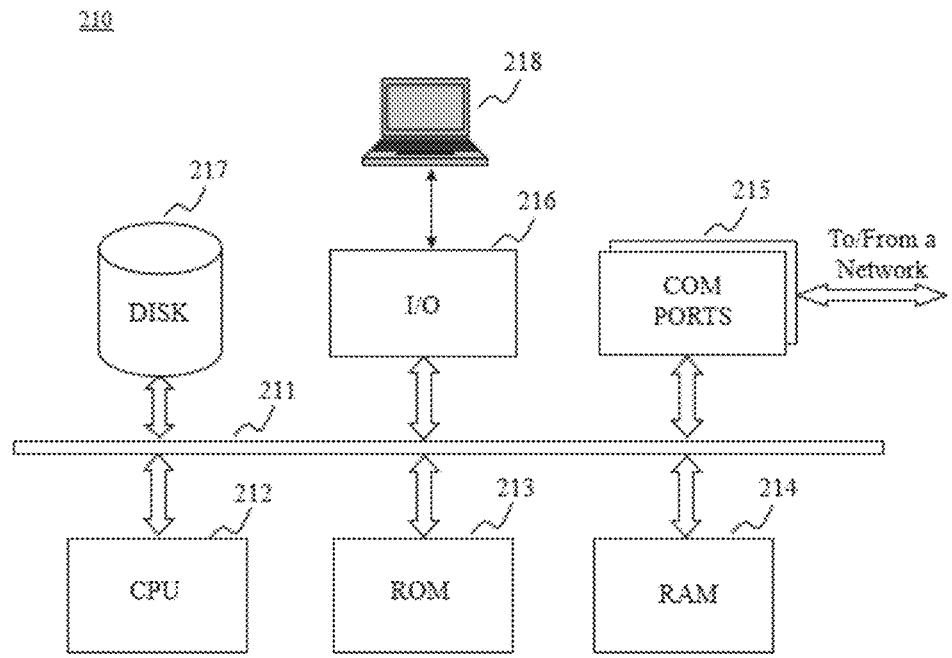
FIG. 2-A
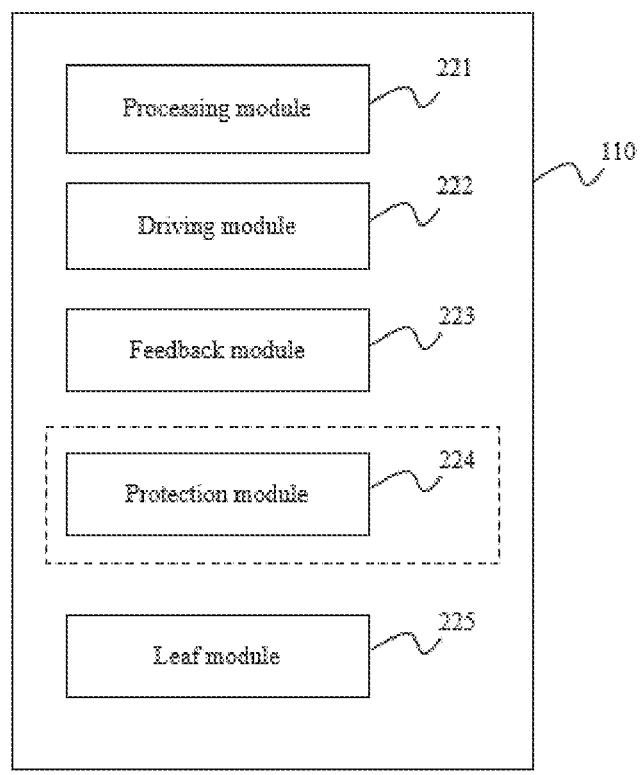
FIG. 2-B

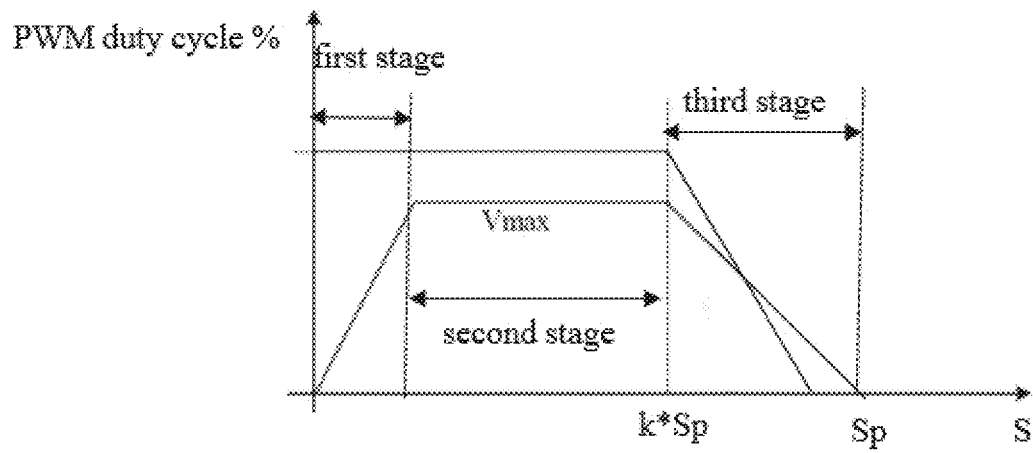
FIG. 4-A
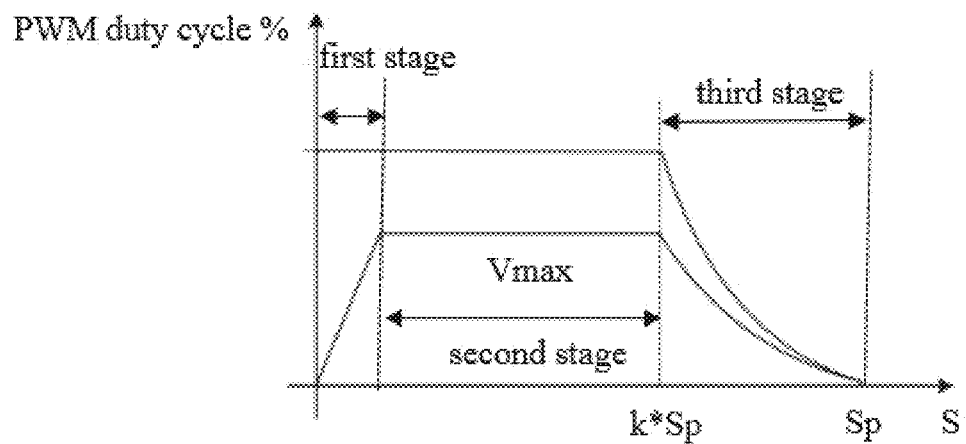
FIG. 4-B

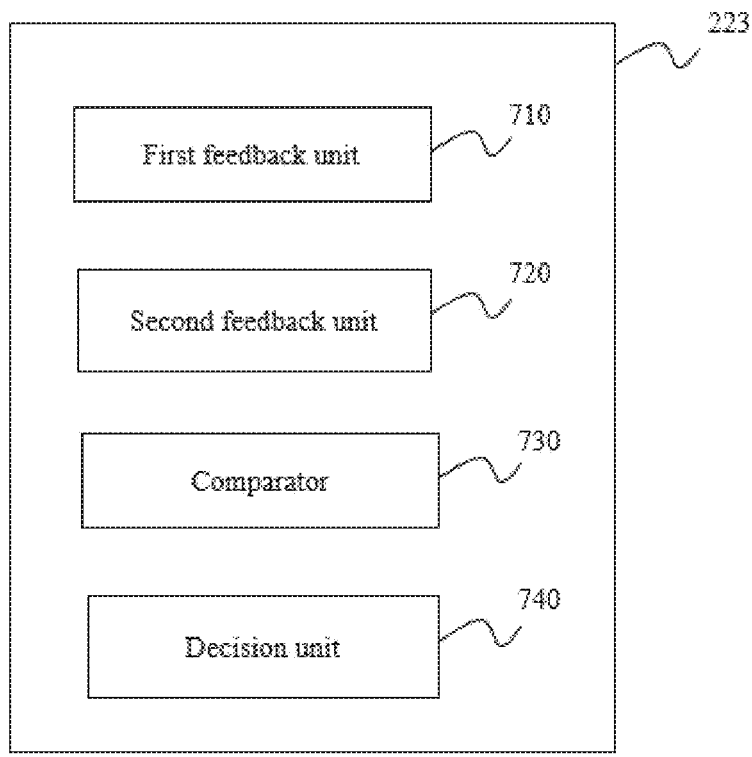
FIG. 7-A
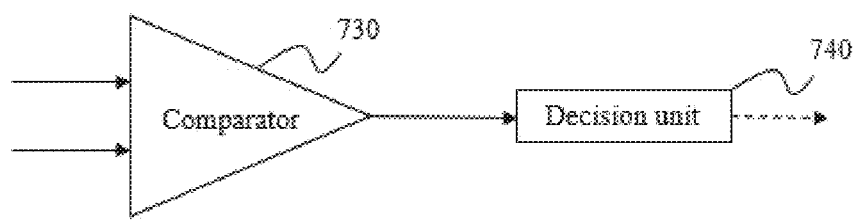
FIG. 7-B

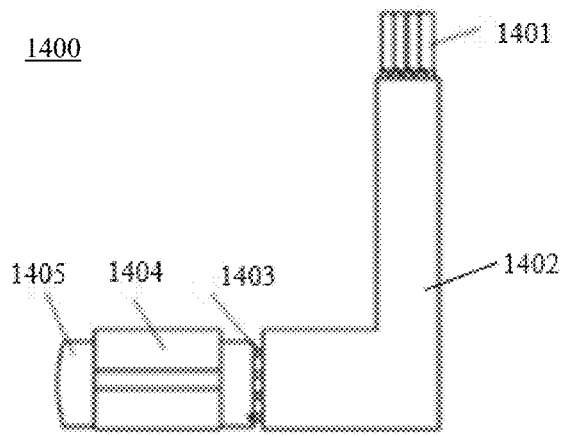
FIG. 14-A
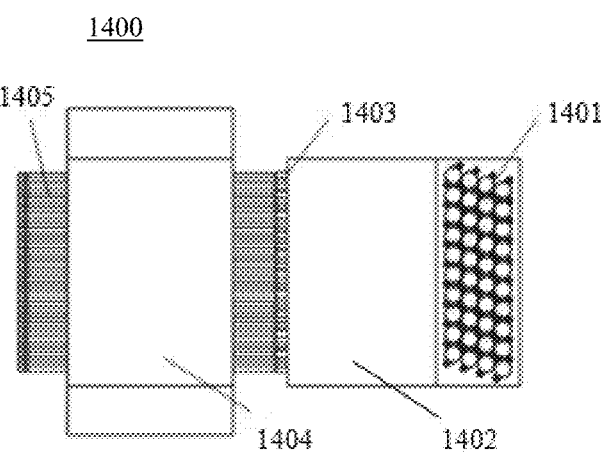
FIG. 14-B

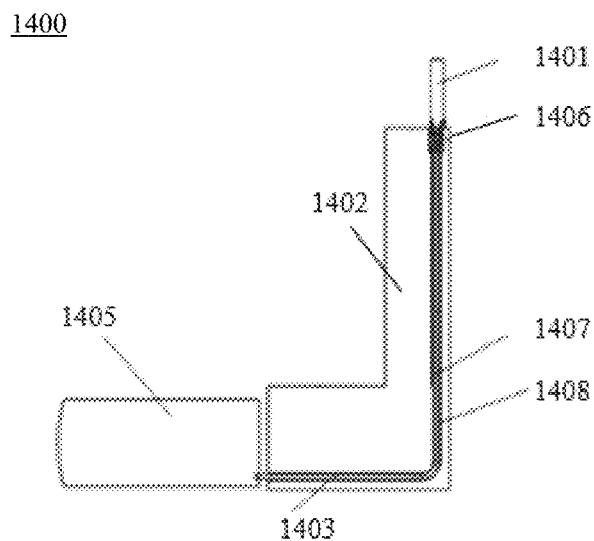
FIG. 14-C
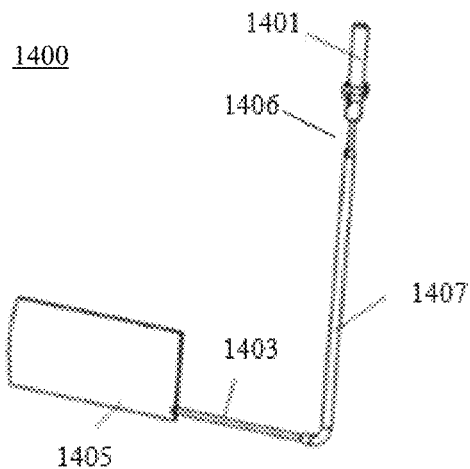
FIG. 14-D

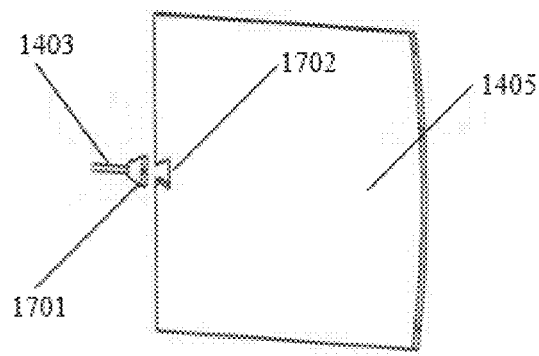
FIG. 17-A
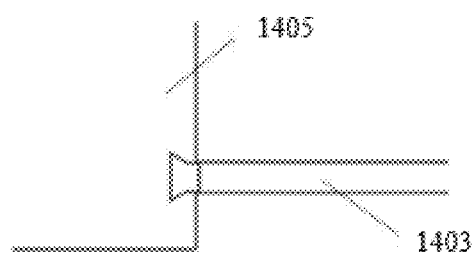
FIG. 17-B
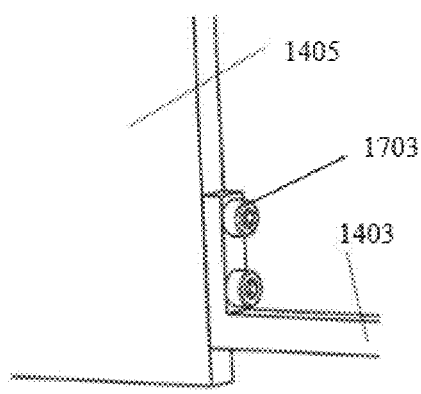
FIG. 17-C

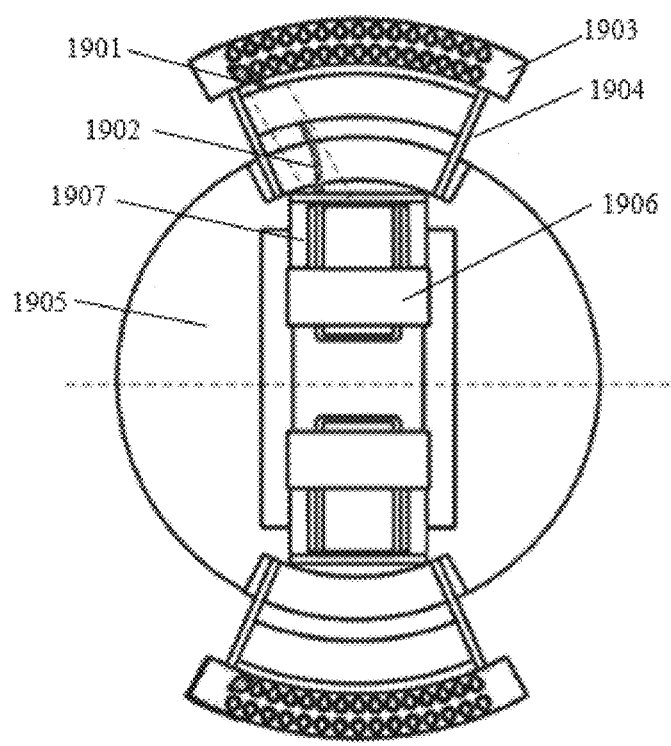
FIG. 19-A
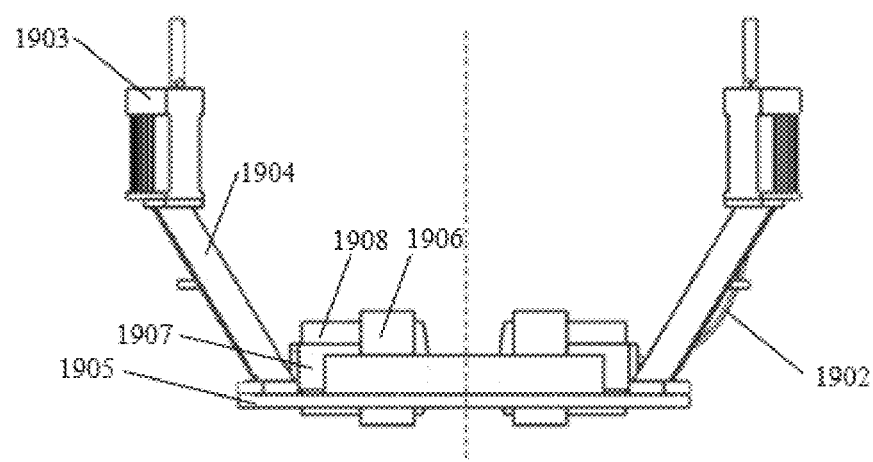
FIG. 19-B

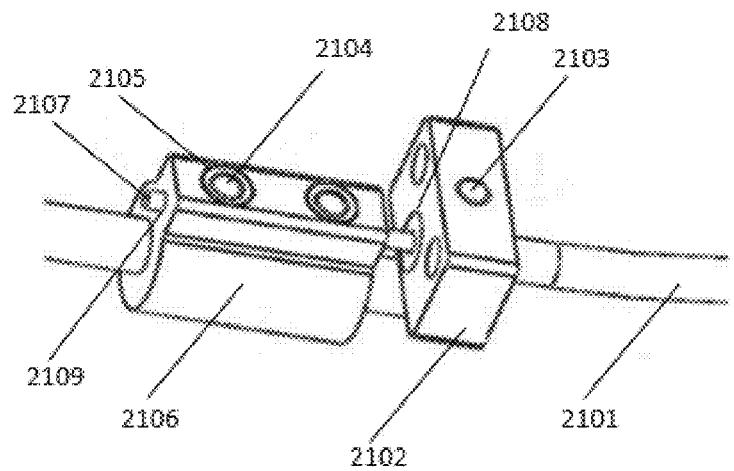
FIG. 21-A
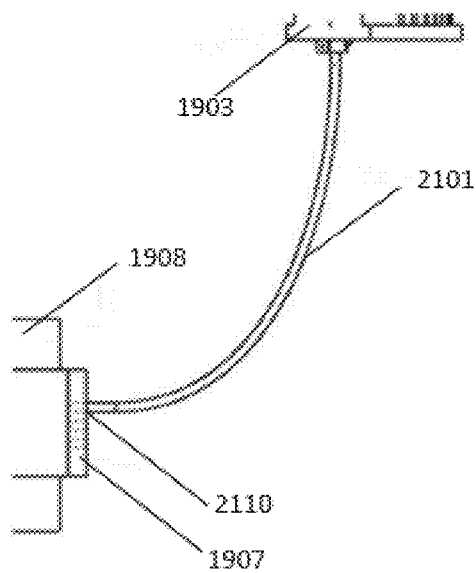
FIG. 21-B

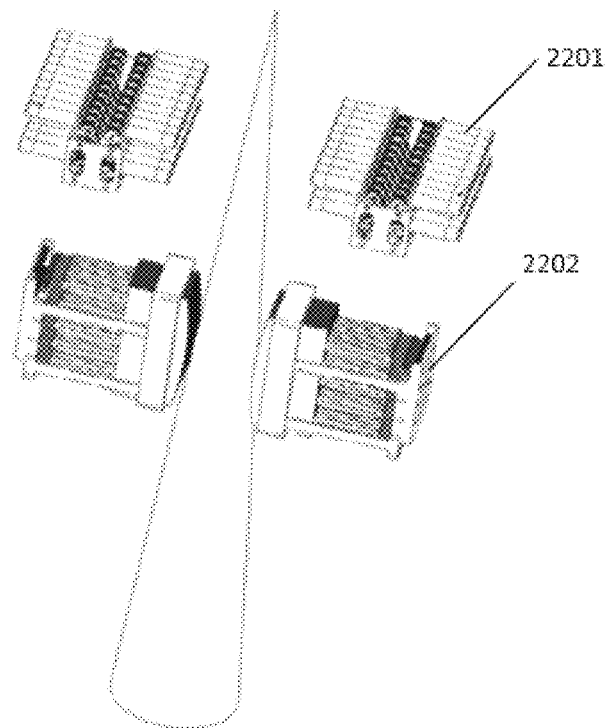
FIG. 22-A
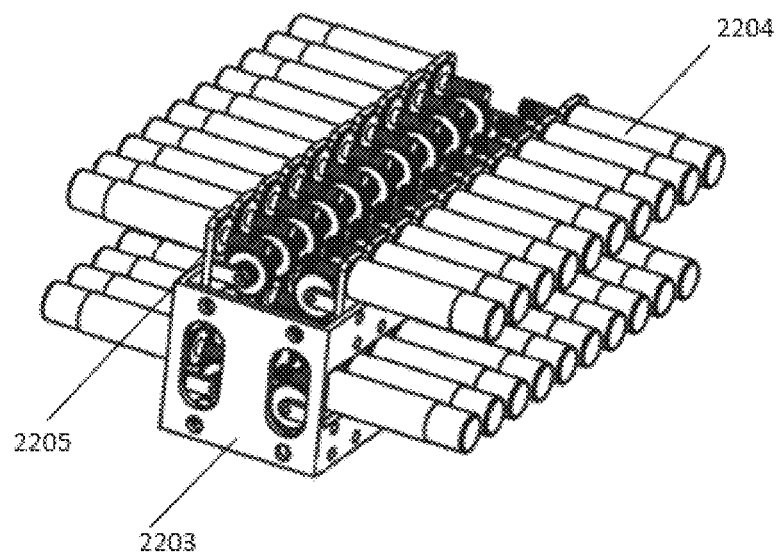
FIG. 22-B

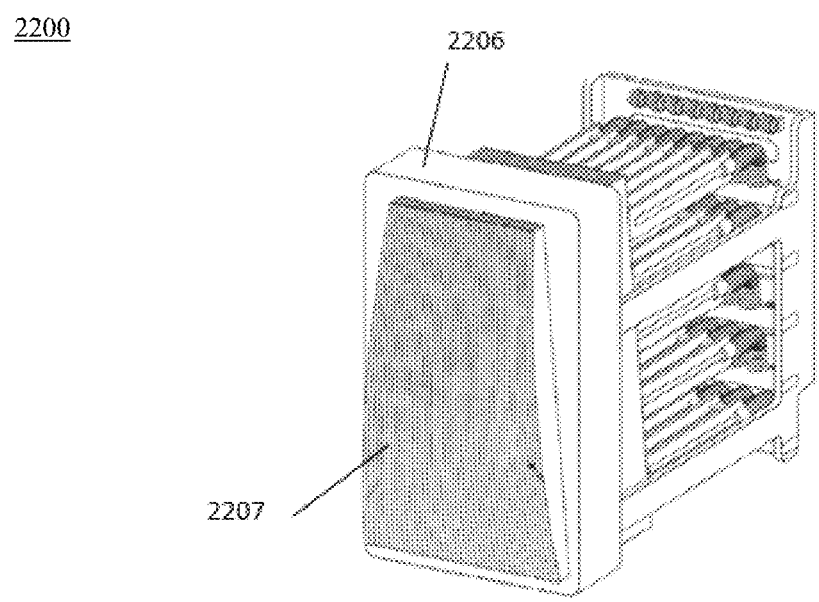
FIG. 22-C

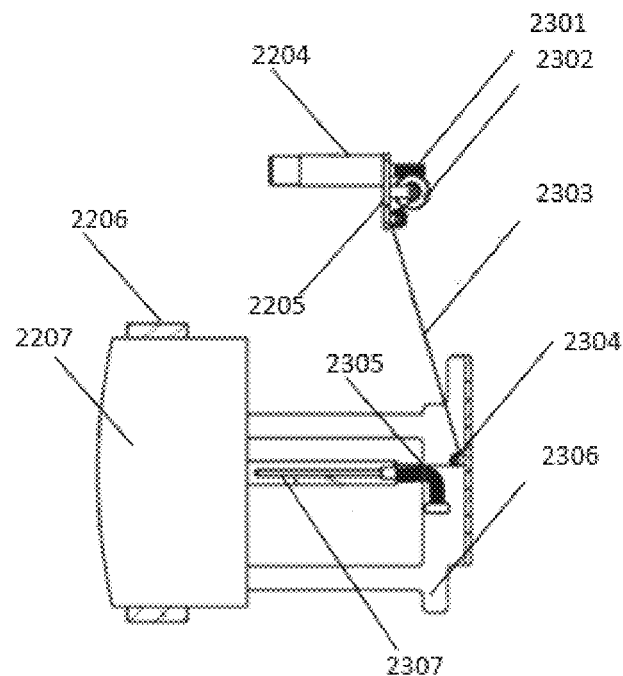
FIG. 23-A
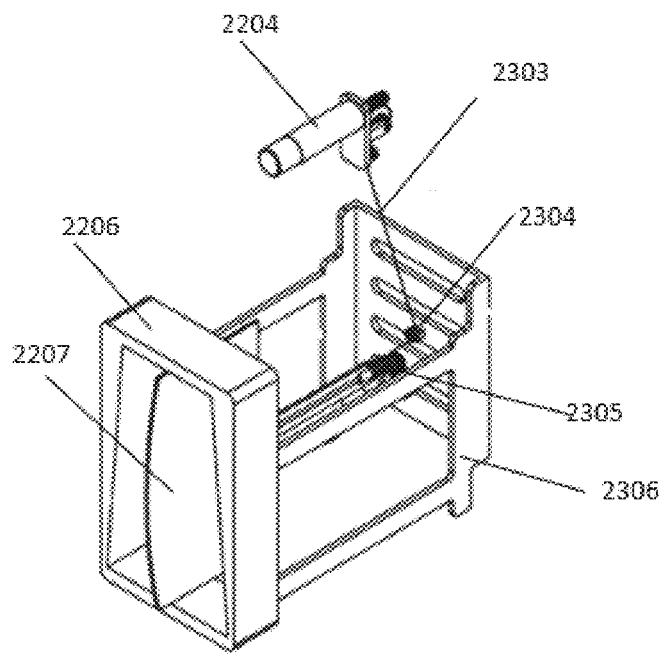
FIG. 23-B

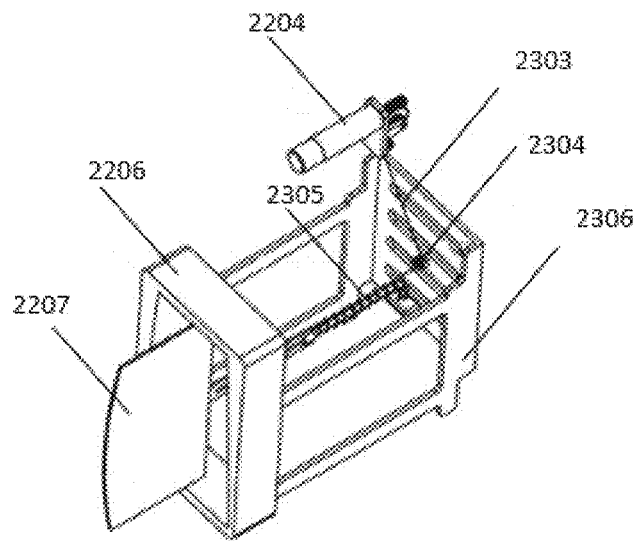
FIG. 23-C
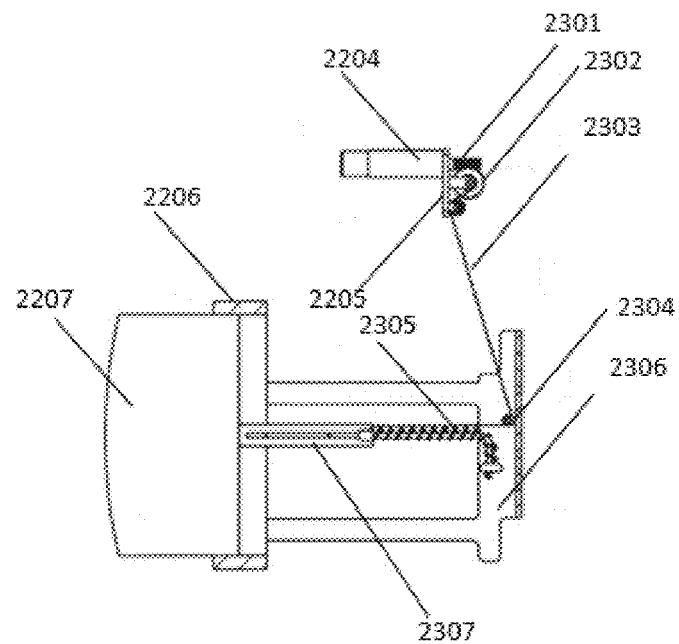
FIG. 23-D

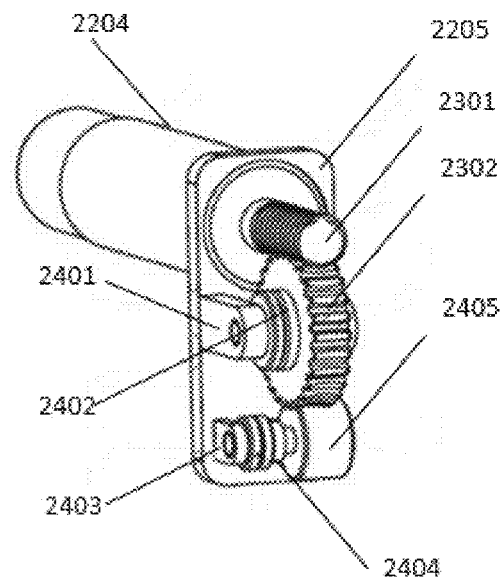
FIG. 24
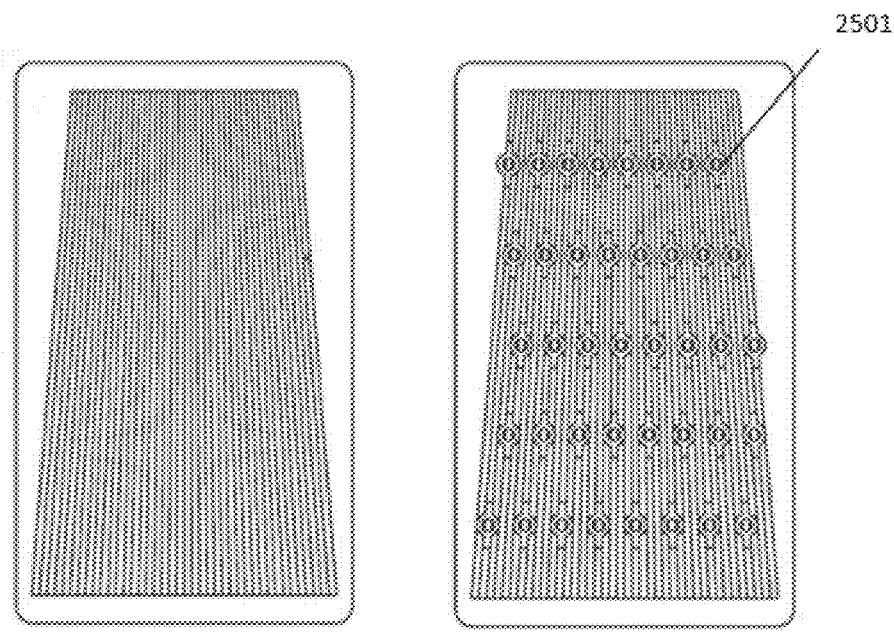
FIG. 25-A        FIG. 25-B

MULTI-LEAF COLLIMATOR AND DRIVING SYSTEM

CROSS-REFERENCE TO RELATED APPLICATIONS

This application is a Continuation of U.S. application Ser. No. 15/313,960, which claims priority of Chinese Patent Application No. 201520698943.6 filed on Sep. 10, 2015 now issued as Chinese Patent No. CN204972723U, Chinese Patent Application No. 201520699659.0 filed on Sep. 10, 2015 now issued as Chinese Patent No. CN204972724U, Chinese Application No. 201510581866.0 filed on Sep. 14, 2015, and Chinese Patent Application No. 201510657060.5 filed on Oct. 12, 2015, the entire contents of each of which are hereby incorporated by reference.

TECHNICAL FIELD

This present disclosure relates to a collimator, and more particularly, relates to a multi-leaf collimator and system for driving the multi-leaf collimator.

BACKGROUND

A multi-leaf collimator (MLC) may be used in shaping a radiation beam used in radiosurgery and radiotherapy (RT). Usually, a multi-leaf collimator is driven by one or more motors. The operation of the motors may be affected by the magnetic field generated by a device nearby. Also, current generated by the motors may tangle the magnetic field and thus affect the device nearby. There is a need to overcome such interferences.

SUMMARY

The present disclosure provided herein relates to a collimator. In some embodiments, the collimator may include a motor, a transmission unit having a first end and a second end, and a leaf unit having a leaf. In some embodiments, the first end of the transmission unit may be connected to the motor and the second end of the transmission unit may be connected to the leaf. In some embodiments, the collimator may be used in a magnetic field, and the transmission unit may reduce interferences between a motor in the collimator and the magnetic field.

In some embodiments, the collimator may further include a shell configured to contain the motor. In some embodiments, the transmission unit may include a transmission shaft. In some embodiments, the collimator may further include a connection unit configured to connect the transmission unit and the leaf. The leaf may have a groove. The connection unit may have an expansion bump. The expansion bump may match the groove.

In some embodiments, the transmission unit may include a transmission line and an elastic piece. The transmission line may provide the leaf a first force, and the elastic piece may provide the leaf a second force. In some embodiments, the elastic piece may be a spring having a third end and a fourth end. The third end of the spring may be fixed, and the fourth end of the spring may be connected to the leaf. The spring may be in a compressed state. In some embodiments, the leaf may have a thickness in a range from 0.8 mm to 2.2 mm.

In some embodiments, the collimator may further include a conversion unit configured to change a rotational motion of the motor to linear motion. In some embodiments, the transmission unit may be flexible. In some embodiments, the conversion unit may include a gear and a worm. The worm may be connected to the motor. The gear may be driven by the worm. In some embodiments, the gear and the worm may be self-locking.

In some embodiments, the collimator may further include a guiding unit configured to control a movement path of the transmission unit. In some embodiments, the collimator may further include a feedback module configured to detect a movement of the leaf.

In another aspect of the present disclosure, a collimator system is provided. In some embodiments, the collimator system may include a leaf module having a leaf, a driving module having a motor configured to drive the leaf, and a processing module to generate a movement profile of the leaf. The movement profile of the leaf may include a first speed during a first stage, a second speed of the leaf during a second stage, and a third speed of the leaf during a third stage. The first speed may increase with time, the second speed may be constant, and the third speed may decrease at a variable rate with time. In some embodiments, the variable rate may be determined based on a distance between a leaf current location and a leaf target location.

In some embodiments, the collimator system may further include a feedback module configured to detect a movement of the leaf. In some embodiments, the feedback module may include a first feedback unit and a second feedback unit. The first feedback unit may be configured to detect the movement of the leaf, and the second feedback unit may be configured to detect a movement of the motor.

In some embodiments, the processing module may detect a status of the leaf based on the movement of the leaf and the movement of the motor. In some embodiments, the leaf module may include a transmission unit. The transmission unit may be connected to the motor and the leaf. In some embodiments, the device may further include a protection module configured to detect whether the motor is running normally.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIG. 2-A illustrates the architecture of a computing device which can be used to realize a specialized system implementing the present teaching;

FIG. 2-B is a block diagram illustrating the collimator system 110 according to some embodiments of the present disclosure;

FIG. 4-A and FIG. 4-B illustrate two exemplary leaf movement profiles according to some embodiments of the present disclosure;

FIG. 7-A is a block diagram of the feedback module 223 according to some embodiments of the present disclosure;

FIG. 7-B is an exemplary diagram of the comparator 730 and the decision unit 740 according to some embodiments of the present disclosure;

FIG. 14-A to FIG. 14-D illustrate an exemplary MLC according to some embodiments of the present disclosure;

FIG. 17-A to FIG. 17-C illustrate exemplary connections between the leaf 1405 and the transmission shaft 1407 according to some embodiments of the present disclosure;

FIG. 19-A to FIG. 19-B illustrate an exemplary MLC according to some embodiments of the present disclosure;

FIG. 21-A and FIG. 21-B illustrate an exemplary immobilization regarding the sleeve 2101 according to some embodiments of the present disclosure;

FIG. 22-A to FIG. 22-C illustrate an exemplary MLC according to some embodiments of the present disclosure;

FIG. 23-A to FIG. 23-D illustrate an exemplary configuration of MLC 2200 according to some embodiments of the present disclosure;

FIG. 24 illustrate details regarding the configuration of the MLC 2200 according to some embodiments of the present disclosure;

FIG. 25-A and FIG. 25-B illustrate an exemplary configuration of the leaves 2207 according to some embodiments of the present disclosure.

DETAILED DESCRIPTION

In the following detailed description, numerous specific details are set forth by way of example in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

It will be understood that the term "system," "device," "apparatus," "unit," "module," "component," and/or "block" used herein are one method to distinguish different components, elements, parts, section or assembly of different level in ascending order. However, the terms may be exchanged or displaced by other expression if they may achieve the same purpose.

It will be understood that when a device, apparatus, unit, module, component or block is referred to as being "on," "connected to" or "coupled to" another device, apparatus, unit, module, component or block, it may be directly on, connected or coupled to, or communicate with the other device, apparatus, unit, module, component or block, or an intervening device, apparatus, unit, module, component or block may be present, unless the context clearly indicates otherwise. As used herein, the term "and/or" includes any and all combinations of one or more of the associated listed items.

The terminology used herein is for the purposes of describing particular examples and embodiments only, and is not intended to be limiting. As used herein, the singular forms "a," "an," and "the" may be intended to include the plural forms as well, unless the context clearly indicates otherwise. It will be further understood that the terms "include," and/or "comprise," when used in this disclosure, specify the presence of integers, devices, behaviors, stated features, steps, elements, operations, and/or components, but do not exclude the presence or addition of one or more other integers, devices, behaviors, features, steps, elements, operations, components, and/or groups thereof. It will be further understood that the terms "construction" and "reconstruction," when used in this disclosure, may represent a similar process in which an image may be transformed from data.

Figure 1:
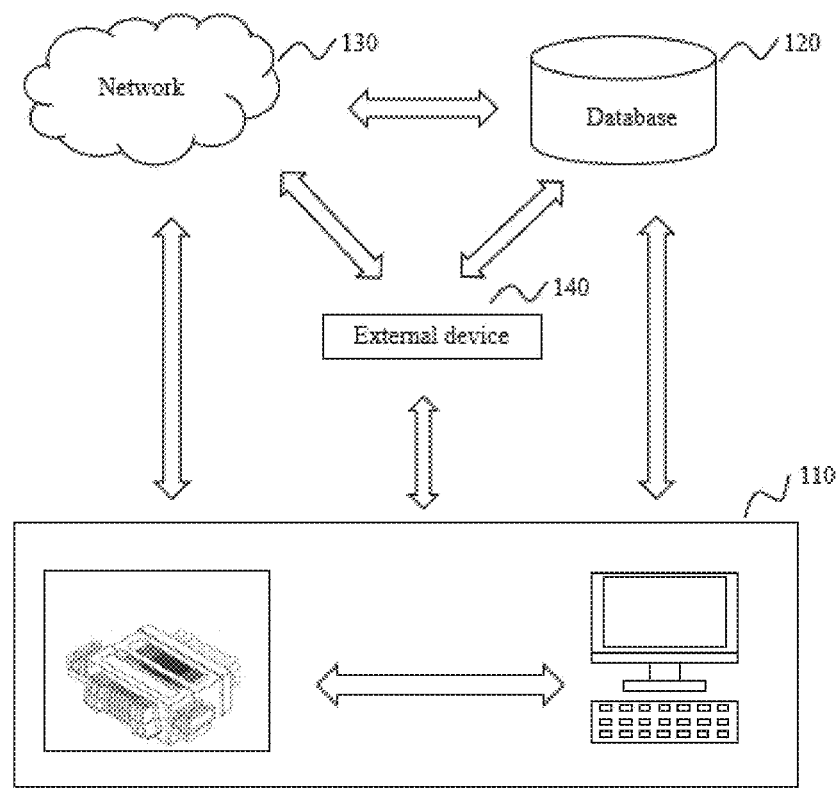
FIG. 1 is a diagram of a radiation therapy platform 100 according to some embodiments of the present disclosure.

FIG. 1 is a diagram of a radiation therapy platform 100 according to some embodiments of the present disclosure. It should be noted that the radiation therapy platform 100 described below is merely provided for illustration purposes, and not intended to limit the scope of the present disclosure. The collimator system may find its applications in different fields, for example, medicine, or industry. For example, the system may be used in Radiotherapy (RT) and Magnetic Resonance-Radiotherapy (MR-RT). As illustrated in FIG. 1, the radiation therapy platform 100 may include a collimator system 110, a database 120, a network 130, an external device 140, and a radiation generating device, such as a linear accelerator (not shown in the figure).

The collimator system 110 may provide conformal shaping of beams by changing the configuration of a leaf of the collimator system 110. For instance, a leaf may be moved in or out of the path of the beams in order to block the beams or allow it to pass through. In some embodiments, the collimator system 110 may include a plurality of leaves. In some embodiments, the plurality of leaves may be independently moved. Merely by way of example, the collimator system 110 may allow the shaping of one or more linear accelerator (LINAC) beams to match the border of a target tumor for conformal radiotherapy. In some embodiments, the collimator system 110 may create various intensity modulated radiation therapy distributions. In some embodiments, the collimator system 110 may include leaf driving system. The leaf driving system may drive the leaves.

The database 120 may store data relating to the radiation therapy platform 100. In some embodiments, the data may include an analog signal and/or a digital signal. Merely by way of example, the database 120 may include a memory. The memory may be a main memory or an assistant memory. The memory may include a Random Access Memory (RAM), a Read Only Memory (ROM), a Complementary Metal Oxide Semiconductor Memory (CMOS), a magnetic surface memory, a Hard Disk Drive (HDD), a floppy disk, a magnetic tape, a disc (CD-ROM, DVD-ROM, etc.), a USB Flash Drive (UFD), or the like, or any combination thereof. Access to the database 120 may be controlled or gated. A user may need an access privilege to access the database 120. Different users may have different access privileges to different data stored in the database 120. For instance, a first user may only read a portion of the data stored in the database 120, a second user may read and revise a portion of the data stored in the database 120, a third user may read all data stored in the database 120, a fourth user may read and revise all data stored in the database 120, and a fifth user has no access privilege and therefore is unable to read or revise any data stored in the database 120. Merely by way of example, the database 120 may be implemented on a cloud platform. The cloud platform may be a cloud computing platform or a cloud storing platform. The type of the cloud platform may include a private cloud, a public cloud, a hybrid cloud, a community cloud, a distributed cloud, an inter-cloud, a multi-cloud, or the like, or any combination thereof.

The network 130 may connect one or more components of the radiation therapy platform 100 with each other, or with an external device (e.g., an external storage device, an external information source, or the like, or a combination thereof). The network 130 may be a single network or a combination of different networks. Merely by way of example, the network 130 may be a tele communications network, a Local Area Network (LAN), a Wireless Local Area Network (WLAN), a Metropolitan Area Network (MAN), a Wide Area Network (WAN), a Bluetooth, a ZigBee, a Near Field Communication (NFC), a public network, a private network, a proprietary network, a Public Telephone Switched Network (PSTN), the Internet, a wireless network, a virtual network, or the like, or any combination thereof.

The external device 140 may be configured to input or receive data to and/or from a user, the network 130, the database 120, the collimator system 110, or the like, or any combination thereof. In some embodiments, the external device 140 may include a user input, a controller, a processor, etc. For example, the user input may be a keyboard input, a mouse input, a touch screen input, a handwritten input, an image input, a voice input, an electromagnetic wave input, or the like, or any combination thereof. The controller may be configured to control the collimator system 110, the database 120, or the network 130. The processor may be configured to process data acquired in the external device 140. In some embodiments, the collimator system 110 and the external device 140 may be integrated as one device. Merely by way of example, the external device 140 may be a computer, a laptop, a Personal Digital Assistant (PDA), a mobile phone, a tablet computer, a portable device, or the like, or any combination thereof.

It should be noted that the above description is merely provided for the purposes of illustration, and not intended to limit the scope of the present disclosure. For persons having ordinary skills in the art, multiple variations and modifications may be made under the teachings of the present disclosure. For example, a radiation therapy platform 100 may include several databases when the collimator system 110 includes several collimators and several processors. As another example, the collimator system 110 may be divided into two independent devices. However, those variations and modifications do not depart from the scope of the present disclosure.

FIG. 2-A illustrates the architecture of a computing device which can be used to realize a specialized system implementing the present teaching. Such a specialized system incorporating the present teaching has a functional block diagram illustration of a hardware platform which includes user interface elements. The computer may be a general purpose computer or a special purpose computer. Both can be used to implement a specialized system for the present teaching. This computer 210 may be used to implement any component of generating and providing signals as described herein. For example, the processing module 221 as illustrated in FIG. 2-B, etc., may be implemented on a computer such as computer 210, via its hardware, software program, firmware, or a combination thereof. Although only one such computer is shown, for convenience, the computer functions relating to generating and providing signals as described herein may be implemented in a distributed fashion on a number of similar platforms, to distribute the processing load.

The computer 210, for example, includes COM ports 215 connected to and from a network connected thereto to facilitate data communications. The computer 210 also includes a central processing unit (CPU) 212, in the form of one or more processors, for executing program instructions. The exemplary computer platform includes an internal communication bus 211, program storage and data storage of different forms, e.g., disk 217, read only memory (ROM) 213, or random access memory (RAM) 214, for various data files to be processed and/or communicated by the computer, as well as possibly program instructions to be executed by the CPU. The computer 210 also includes an I/O component 216, supporting input/output flows between the computer and other components therein such as user interface elements 218. The computer 210 may also receive programming and data via network communications.

Hence, aspects of the methods of controlling the movement of a leaf and/or other processes, as outlined above, may be embodied in programming. Program aspects of the technology may be thought of as "products" or "articles of manufacture" typically in the form of executable code and/or associated data that is carried on or embodied in a type of machine readable medium. Tangible non-transitory "storage" type media include any or all of the memory or other storage for the computers, processors, or the like, or associated modules thereof, such as various semiconductor memories, tape drives, disk drives and the like, which may provide storage at any time for the software programming.

All or portions of the software may at times be communicated through a network such as the Internet or various other telecommunication networks. Such communications, for example, may enable loading of the software from one computer or processor into another, for example, from a management server or host computer of collimator into the hardware platform(s) of a computing environment or other system implementing a computing environment or similar functionalities in connection with controlling the movement of a leaf. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to tangible "storage" media, terms such as computer or machine "readable medium" refer to any medium that participates in providing instructions to a processor for execution.

Hence, a machine-readable medium may take many forms, including but not limited to, a tangible storage medium, a carrier wave medium or physical transmission medium. Non-volatile storage media include, for example, optical or magnetic disks, such as any of the storage devices in any computer(s) or the like, which may be used to implement the system or any of its components as shown in the drawings. Volatile storage media include dynamic memory, such as a main memory of such a computer platform. Tangible transmission media include coaxial cables; copper wire and fiber optics, including the wires that form a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a physical processor for execution.

Those skilled in the art will recognize that the present teachings are amenable to a variety of modifications and/or enhancements. For example, although the implementation of various components described above may be embodied in a hardware device, it may also be implemented as a software only solution—e.g., an installation on an existing server. In addition, controlling the movement of a leaf including generating and providing signals as disclosed herein may be implemented as a firmware, firmware/software combination, firmware/hardware combination, or a hardware/firmware/software combination.

While the foregoing has described what are considered to constitute the present teachings and/or other examples, it is understood that various modifications may be made thereto and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

FIG. 2-B is a block diagram illustrating the collimator system 110 according to some embodiments of the present disclosure. As illustrated in FIG. 2-B, the collimator system 110 may include a processing module 221, a driving module 222, a feedback module 223, and a leaf module 225. In some embodiments, the collimator system 110 may further include a protection module 224.

The processing module 221 may control the movement of a leaf according to a leaf movement profile. The leaf movement profile may include the speed and/or the time of the leaf movement. In some embodiments, the leaf movement profile may be a movement profile of the motor. In some embodiments, the processing module 221 may determine the leaf movement profile according to parameters including, for example, leaf location information, and time associated with the leaf location information. In some embodiments, the leaf location information may include leaf zero location, leaf initial location, leaf current location, leaf target location, or the like, or a combination thereof. The leaf zero location may be a fixed or predetermined location of a leaf when the collimator system 110 is initialized. In some embodiments, the leaf initial location may be set as leaf zero location. The leaf target location may be determined based on a desired conformal shaping radiation. In some embodiments, information regarding a desired conformal shaping radiation information may be provided by a user by way of, for example, manual input. In some embodiment, information regarding desired conformal shaping radiation may be provided by detection equipment. Detection equipment may include, for example, a digital subtraction angiography (DSA) system, a magnetic resonance imaging (MM) system, a magnetic resonance angiography (MRA) system, a computed tomography (CT) system, a computed tomography angiography (CTA) system, an ultrasound scanning (US) system, a positron emission tomography (PET) system, a single-photon emission computerized tomography (SPECT) system, a CT-MR system, a CT-PET system, a CT-SPECT system, a DSA-MR system, a PET-MR system, a PET-US system, a SPECT-US system, a TMS (transcranial magnetic stimulation)-MR system, a US-CT system, a US-MR system, an X-ray-CT system, an X-ray-MR system, an X-ray-portal system, an X-ray-US system, a Video-CT system, a Video-US system, or the like, or any combination thereof.

In some embodiments, the processing module 221 may determine the leaf current location of the leaf according to the leaf initial location and leaf displacement. The leaf displacement, as used herein, may refer to a distance from the leaf initial location to the leaf current location. In some embodiments, the leaf displacement may be acquired by the feedback module 223. In some embodiments, the processing module 221 may generate a driving signal and/or a warning signal to achieve the leaf movement profile. In some embodiments, the driving signal may include a Pulse Width Modulation (PWM) signal, a start signal, a stop signal, or the like, or any combination thereof. In some embodiments, the PWM signal may control the leaf movement. In some embodiments, the start/stop signal may start/stop a motor in the driving module 222. In some embodiments, the warning signal may be used to signal a status of the collimator system 110. For example, a warning signal may be generated by the process module 221 when the motor in the driving module 222 fails. Details regarding the processing module 221 will be further explained in connection with FIG. 3 and FIG. 4.

The driving module 222 may control the movement of a leaf based on a signal from the processing module 221. In some embodiments, the driving module 222 may control the movement of the leaf movement by driving the motor operationally connected to the leaf. Details regarding the driving module 222 will be further explained in connection with FIG. 5 and FIG. 6.

The feedback module 223 may determine the leaf displacement. In some embodiments, the feedback module 223 may determine whether the leaf movement is normal according to the leaf displacement. For instance, the leaf movement may be considered abnormal if the leaf moves out of an acceptable range, beyond a target location, etc. The feedback module 223 may transmit the leaf displacement information to the processing module 221. In some embodiments, the feedback module 223 may be placed on the driving module 222 and/or the leaf module 225. Details regarding the feedback module 223 will be further explained in connection with FIG. 7-A and FIG. 7-B.

The protection module 224 may monitor the working condition of the motor with reference to a monitor signal. In some embodiments, the working conditions may include the operation status, the aging of the motor, or the like, or a combination thereof. In some embodiments, the monitor signal may include a motor current threshold, a motor voltage threshold, or the like, or the combination thereof. Details regarding the protection module 224 will be further explained in connection with FIG. 8.

The leaf module 225 may conformally shape beams from an emitter. In some embodiments, the emitter may be a cobalt-60 therapy instrument, an X knife, a y knife, a medical linear accelerator, and a proton accelerator, etc. In some embodiments, the leaf module 225 may include a collimator, for example, a multi-leaf collimator. Details regarding the leaf module 225 will be further explained in connection with FIG. 9.

It should be noted that the above description is merely provided for the purposes of illustration, and not intended to limit the scope of the present disclosure. For persons having ordinary skills in the art, multiple variations and modifications may be made under the teachings of the present disclosure. For example, the collimator system 110 may further include a storage module that may store signals and the leaf location information, etc. As another example, whether the movement of the leaf is normal may be performed by the processing module 221. As a further example, the processing module 221, the driving module 222, the feedback module 223, and the protection module 224 may be implemented in the leaf module 225. As still a further example, the protection module 224 may be unnecessary and removed. However, those variations and modifications do not depart from the scope of the present disclosure.

Figure 3:
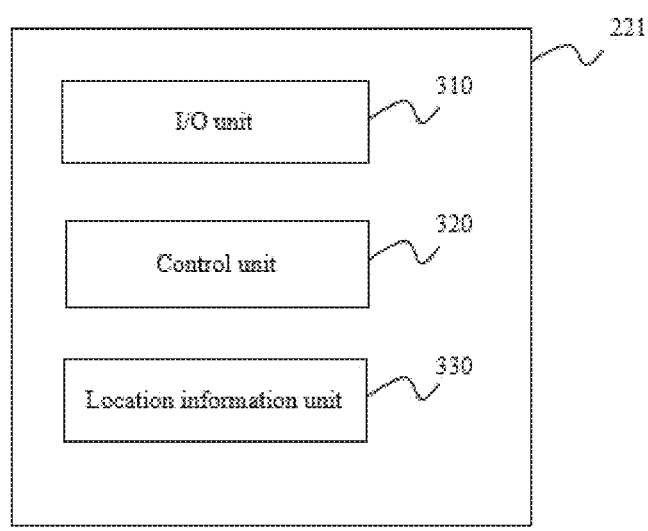
FIG. 3 is a block diagram of the processing module 221 according to some embodiments of the present disclosure.

FIG. 3 is a block diagram of the processing module 221 according to some embodiments of the present disclosure. The processing module 221 may include an I/O unit 310, a control unit 320, and a location information unit 330. In some embodiments, the processing module 221 may the computer 210.

The I/O unit 310 may acquire and transmit a signal. In some embodiments, the I/O unit 310 may be the I/O component 216. In some embodiments, the I/O unit 310 may acquire a leaf target location. In some embodiments, the leaf target location may be provided by a user, or retrieved from a master computer. The master computer may be a computer which may output control instructions to the collimator system 110. In some embodiments, the leaf target location may be determined according to a treatment region acquired by the I/O unit 310. In some embodiments, the I/O unit 310 may acquire information regarding a leaf displacement from the feedback module 223. In some embodiments, the I/O unit 310 may acquire a monitor signal from the protection module 224. In some embodiments, the I/O unit 310 may transmit a warning signal to the user. In some embodiments, the I/O unit 310 may transmit a driving signal to the driving module 222.

The control unit 320 may determine the leaf movement profile. In some embodiments, the control unit 320 may be COM ports 215. In some embodiments, the control unit 320 may determine the leaf movement profile according to the leaf location information and leaf location offset acquired from the location information unit 330. The leaf location offset as used herein may be a difference between the leaf target location and the leaf current location. Details regarding the leaf location offset will be further explained below.

In some embodiments, the leaf movement profile may include three stages in a round of operation. A round of operation, as used herein, may be an operation for a leaf to move from a location (e.g., an initial position, etc.) to the leaf target location. For the purposes of illustration, the three stages may be marked as a first stage, a second stage, and a third stage, respectively; the time for each stage may be marked as a first time period, a second time period, and a third time period, respectively. In some embodiments, the time periods of the three stages may be set according to factors including, for example, the leaf target location, the distance the leaf needs to travel to reach the leaf target location, or the like, or a combination thereof. For example, the third time period may be set to be a percentage of the time for a round of operation. In some embodiments, the percentage of the third time period in the round of operation may be from 10% to 30%, such as, 5%, 10%, 15%, 20%, 25%, etc. In some embodiments, the leaf speed may increase in the first stage, constant in the second stage, and decrease in the third stage. In some embodiments, the leaf speed may decrease at a constant rate (or slope) or at a variable rate (or slope). Details regarding the leaf location offset will be further explained in connection with FIG. 4A and FIG. 4B.

In some embodiments, the control unit 320 may generate and/or transmit PWM signals to the driving module 222. Different PWM signals may have different duty cycles. As used herein, a duty cycle may be the percentage of a period in which a PWM signal is active or the power is on. PWM signals with different duty cycles may control the output of the motor in the driving module 222. In some embodiments, the output of the motor may relate to the leaf speed. For instance, different output of the motor may be associated with different leaf speeds.

The location information unit 330 may calculate the leaf location offset. In some embodiments, the leaf location offset may be described as below:

$$E = S_P - S_{enc}, \quad (1)$$

where E may denote the leaf location offset, $S_P$ may denote the leaf target location, and $S_{enc}$ may denote the leaf current location.

In some embodiments, the leaf location offset E may be compensated by a correction factor. In some embodiments, the correction factor may compensate, at least partially, for the leaf location offset relating to the mechanical inertia. The compensated leaf location offset $E_m$ may be described as below:

$$E_m = S_P - S_{enc} - V_t * T_m, \quad (2)$$

where $E_m$ may denote the modified leaf location offset, $S_P$ may denote the leaf target location, $S_{enc}$ may denote the leaf current location, $V_t * T_m$ may denote the correction factor, $V_t$ may denote the real-time speed of the motor, and $T_m$ may denote the electrical and mechanical time constant of the motor.

It should be noted that the above description is merely provided for the purposes of illustration, and not intended to limit the scope of the present disclosure. For persons having ordinary skills in the art, multiple variations and modifications may be made under the teachings of the present disclosure. For example, the processing module 221 may further include a storage unit that may store signals and the leaf location information, etc. As another example, the control unit 320 and the location information unit 330 may be integrated into one unit. As a further example, the control unit 320 may determine whether the movement of the leaf is normal according to the leaf current location. However, those variations and modifications do not depart from the scope of the present disclosure.

FIG. 4A and FIG. 4B illustrate two exemplary leaf movement profiles according to some embodiments of the present disclosure. It should be noted that the leaf initial location in the figures may be the leaf zero location. Then the leaf current location is the leaf displacement. As shown in each of FIG. 4A and FIG. 4B, the vertical ordinate is the PWM duty cycle and the leaf speed, and the horizontal ordinate is the leaf current location S which is equivalent of the leaf displacement. In some embodiments, the leaf initial location may be different from the leaf zero location. The first stage and the second stage corresponds to an initial PWM duty cycle. The initial PWM duty cycle may be set according to the leaf target location. In some embodiments, the initial PWM duty cycle may be 80% or 90%.

In FIG. 4A and FIG. 4B, the leaf speed may increase in the first stage until the leaf speed reaches $V_{max}$, the leaf speed remains constant at $V_{max}$ in the second stage, and the leaf speed may decrease in the third stage until the leaf speed reaches 0. The leaf may reach the leaf target location at the end of the third stage. $V_{max}$, as used herein, may be the leaf maximum speed in a round of operation. $V_{max}$ may be proportional to the initial PWM duty cycle. In some embodiments, the $V_{max}$ may be set according to the leaf target location. In some embodiments, the $V_{max}$ may be the rated speed of the motor in the driving module 222. In some embodiments, the $V_{max}$ may be obtained through average speed of the leaf in a control period. The control period may relate to the control of the motor. In some embodiments, the average speed of the leaf may be calculated by the distance difference between the leaf location at the start point and the leaf location at the end point the leaf travels within a control period divided by the duration of the control period. As shown in FIG. 4A and FIG. 4B, the leaf current location at the end point of the second stage may be marked as k*Sp, where k may denote a constant which is less than one, and Sp may denote the leaf target location. In some embodiments, k may be 0.8, or 0.85, or 0.9, etc.

In FIG. 4A, the PWM duty cycle may start to decrease at $k*S_P$ with a constant slope. The leaf speed may start to decrease correspondingly at $k*S_P$. In some embodiments, the constant slope may be determined by $V_{max}$ divided by T, where T is an electrical and mechanical time constant of the motor. T may also be referred to as $T_m$ as in Equation (5).

In FIG. 4B, the PWM duty cycle may start to decrease at $k*S_P$ with a variable slope. The leaf speed may start to decrease correspondingly at $k*S_P$. In some embodiments, the variable slope may be determined based on, for example, the remaining distance the leaf needs to move to reach the leaf target location $S_P$ and the time available for the movement. The remaining distance, as used herein, may be the distance between the leaf current location S and the leaf target location $S_P$. In some embodiments, the variable slope may decrease as the remaining distance decreases. The dynamic slope of the PWM duty cycle may be described as below:

$$P(S_P)=b*(S-S_P)^2, \quad (3)$$

where $P(S_P)$ may denote the variable slope of the PWM duty cycle, S may denote the leaf current location, $S_P$ may denote the leaf target location, and b is described as below:

$$b=(1-k)^2*S/p, \quad (4)$$

where k may denote a constant that is less than one, S may denote the leaf current location, P may denote the PWM duty cycle when the motor in the driving module 222 is running with the rated speed.

In some embodiments, the dynamic slope of the PWM duty cycle $P(S_P)$ may be modified according to Equation (2), which may be described as below:

$$P(S_P)=b*(S-S_P-V_t*T_m)^2, \quad (5)$$

where P ($S_P$) may denote the dynamic slope of the PWM duty cycle, b is described as Equation (4), S may denote the leaf current location, $S_P$ may denote the leaf target location, $V_t$ may denote the real-time speed of the motor, and $T_m$ may denote the electrical and mechanical time constant of the motor.

Figure 5:
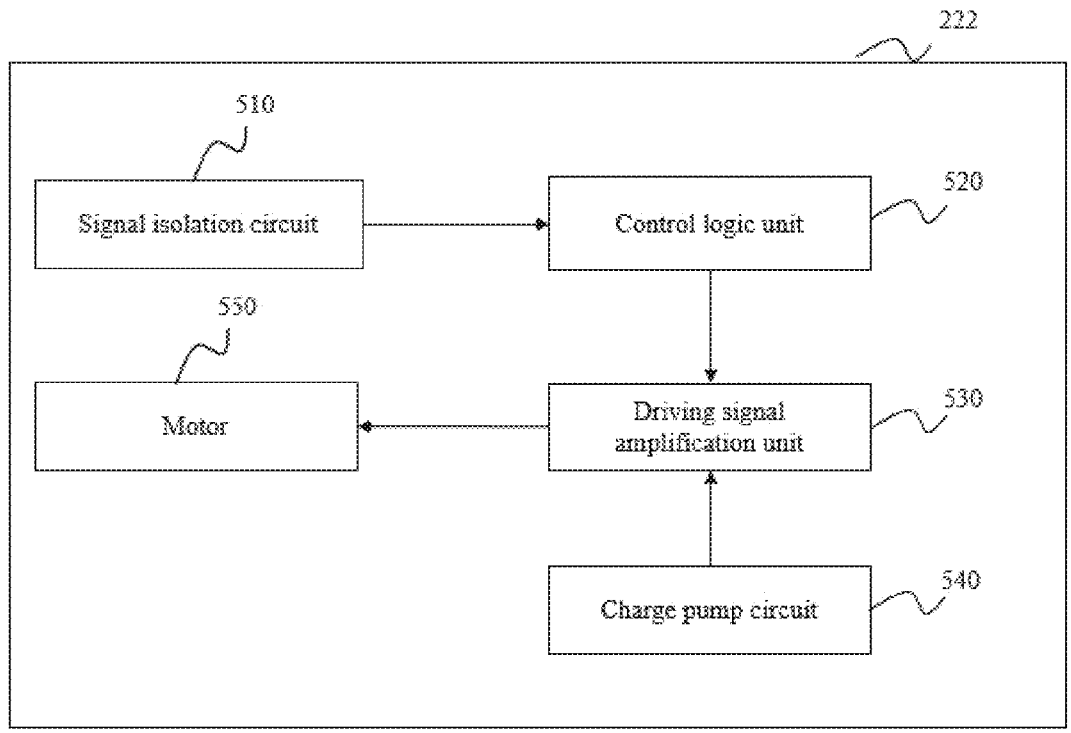
FIG. 5 is a block diagram of the driving module 222 according to some embodiments of the present disclosure.

FIG. 5 is a block diagram of the driving module 222 according to some embodiments of the present disclosure. The driving module 222 may include a signal isolation circuit 510, a control logic unit 520, a driving signal amplification unit 530, a charge pump circuit 540, and a motor 550.

The signal isolation circuit 510 may reduce influence of noise on the control unit 320. In some embodiments, the signal isolation circuit 510 may be a photoelectric isolation circuit. In some embodiments, the signal isolation circuit 510 may acquire a driving signal from the processing module 221. The driving signal may be a power signal. The control logic unit 520 may conduct a logic operation based on the driving signal. In some embodiments, the logic relationship operation may be an AND operation between an enable signal and the driving signal. The driving signal amplification unit 530 may amplify the driving signal. In some embodiments, the amplified driving signal may drive the motor 550. In some embodiments, the driving signal amplification unit 530 may include an H bridge driver with one or more N field effect transistors. The gate voltage may be greater than the drain voltage when an N field effect transistors start. The charge pump circuit 540 may increase the gate voltage so that the gate voltage may be greater than the drain voltage. The motor 550 may drive the leaf in the leaf module 225. Exemplary motors may include a rotating motor, a linear motor, etc. As used herein, the linear motor may convert electric energy to mechanical energy in the form of a linear movement.

Figure 6:
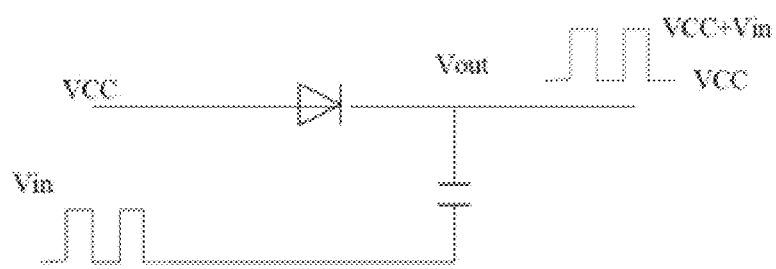
FIG. 6 is an exemplary circuit of the charge pump circuit 540 according to some embodiments of the present disclosure.

FIG. 6 is an exemplary circuit of the charge pump circuit 540 according to some embodiments of the present disclosure. As shown in FIG. 6, Vin may be a square-wave signal. Vin may be amplified though Volt Current Condenser (VCC). Vout may be the sum of Vin and VCC. Vout may be the amplified square-wave signal.

FIG. 7-A is a block diagram of the feedback module 223 according to some embodiments of the present disclosure. The feedback module 223 may include a first feedback unit 710, a second feedback unit 720, a comparator 730, and a decision unit 740.

The first feedback unit 710 may detect the leaf displacement. For the purposes of illustration, the leaf displacement detected by the first feedback unit 710 may be marked as the first leaf displacement A. In some embodiments, the first feedback unit 710 may be placed on the motor 550 in the driving module 222, or the guiding unit 930 in the leaf module 225, or the leaf unit 940 in the leaf module 225, or a combination thereof. Merely by way of example, the first feedback unit 710 may be placed on the guiding unit 930 in the leaf module 225 and the leaf unit 940 in the leaf module 225.

In some embodiments, the first feedback unit 710 may be a linear encoder displacement transducer including a grating ruler and a corresponding grating ruler reading head. The grating ruler may be placed on the top side of the leaf in the leaf unit 940. The corresponding grating ruler reading head may be placed on the interior of the guiding box in the leaf unit 940. The interior may be opposite, with respect to the top side of the leaf. The top side of the leaf, as used herein, may be the top side of the leaf along the horizontal movement of the leaf. In some embodiments, the location of the corresponding grating ruler reading head may be opposite, with respect to the location of the grating ruler. In some embodiments, the grating ruler displacement transducer may detect the first leaf displacement according to the movement of the grating ruler relative to the grating ruler reading head.

In some embodiments, the first feedback unit 710 may be a magnetic encoder displacement transducer including magnetic elements and corresponding magnetic element reading pieces. In some embodiments, the magnetic element may be a bar magnet, and the magnetic element reading piece may be a hall sensor. The magnetic elements may be placed on the top side of the leaf in the leaf unit 940. The corresponding magnetic element reading pieces may be placed on the interior of guiding box in the leaf unit 940. The interior may be opposite, with respect to the top side of the leaf. The top side of the leaf, as used herein, may be the top side of the leaf along the horizontal movement of the leaf. In some embodiments, the location of the magnetic element reading pieces may be opposite, with respect to the location of the magnetic elements. In some embodiments, the magnetic encoder displacement transducer may detect the first leaf displacement according to the movement of the magnetic elements relative to the corresponding magnetic element reading pieces. As an example, the corresponding magnetic element reading pieces may detect the variation of the magnetic field and output a pulse signal; the first leaf displacement may be calculated based on the pulse signal.

In some embodiments, the first feedback unit 710 may be an encoder or a potentiometer. The encoder/potentiometer may be placed on the motor 550, such as a shaft of the motor 550, the guiding wheel in the guiding unit 930, the reeling wheel in the guiding unit 930, etc. In some embodiments, the encoder and/or potentiometer may detect the first leaf displacement according to number of rounds the motor 550, or the guiding wheel, or the reeling wheel rotates.

The second feedback unit 720 may detect the leaf displacement. For the purposes of illustration, the leaf displacement detected by the second feedback unit 720 may be marked as the second leaf displacement B. In some embodiments, the second feedback unit 720 may include the same displacement transducers as the first feedback unit 710. In some embodiments, the second feedback unit 720 may include different displacement transducers than the first feedback unit 710. In some embodiments, the second feedback unit 720 may be placed at the same or similar location as the first feedback unit 710. In some embodiments, the second feedback unit 720 may be placed at a different location than the first feedback unit 710.

The comparator 730 may compare the first leaf displacement A and the second leaf displacement B. In some embodiments, the comparator 730 may determine the difference between A and B, a multiple of |A-B| and A, a multiple of |A-B| and B, etc. For the purposes of illustration, the difference between A and B may be marked as C, the multiple of |A-B| and A may be marked as D, and the multiple of |A-B| and B may be marked as E. In some embodiments, the comparator 730 may further compare C, and/or D, and/or E with a threshold, respectively. The comparator 730 may transmit the comparison result to the decision unit 740.

The decision unit 740 may determine whether the movement of the leaf is normal according to the comparison result acquired from the comparator 730. As an example, the comparison result may be that D is less than the threshold, or that D is not less than the threshold. In some embodiments, the threshold may be 5%. When the comparison result is that D is less than 5%, the decision unit 740 may determine that the movement of the leaf is normal; when the comparison result is that D is not less than 5%, the decision unit 740 may determine that the movement of the leaf is abnormal. The decision unit 740 may transmit the determination result to the processing module 221.

It should be noted that the above description is merely provided for the purposes of illustration, and not intended to limit the scope of the present disclosure. For persons having ordinary skills in the art, multiple variations and modifications may be made under the teachings of the present disclosure. For example, the feedback module 223 may further include a storage unit configured to store the leaf displacement, the comparison result, the determination result, etc. As another example, the comparator 730 and the decision unit 740 may be unnecessary and removed from the control unit 320. However, those variations and modifications do not depart from the scope of the present disclosure.

FIG. 7-B is an exemplary diagram of the comparator 730 and the decision unit 740 according to some embodiments of the present disclosure. Leaf displacement acquired by the first feedback unit 710 and the second feedback unit 720 may be provided to the comparator 730. The comparator 730 may compare the difference between the leaf displacement measured by the first feedback unit 710 and the leaf displacement measured by the second feedback unit 720. The decision unit 740 may determine whether the movement of the leaf is normal according to the comparison result acquired from the comparator 730. Details regarding the comparator 730 and the decision unit 740 may be found elsewhere in the present disclosure, for example, in the description of FIG. 7-A.

Figure 8:
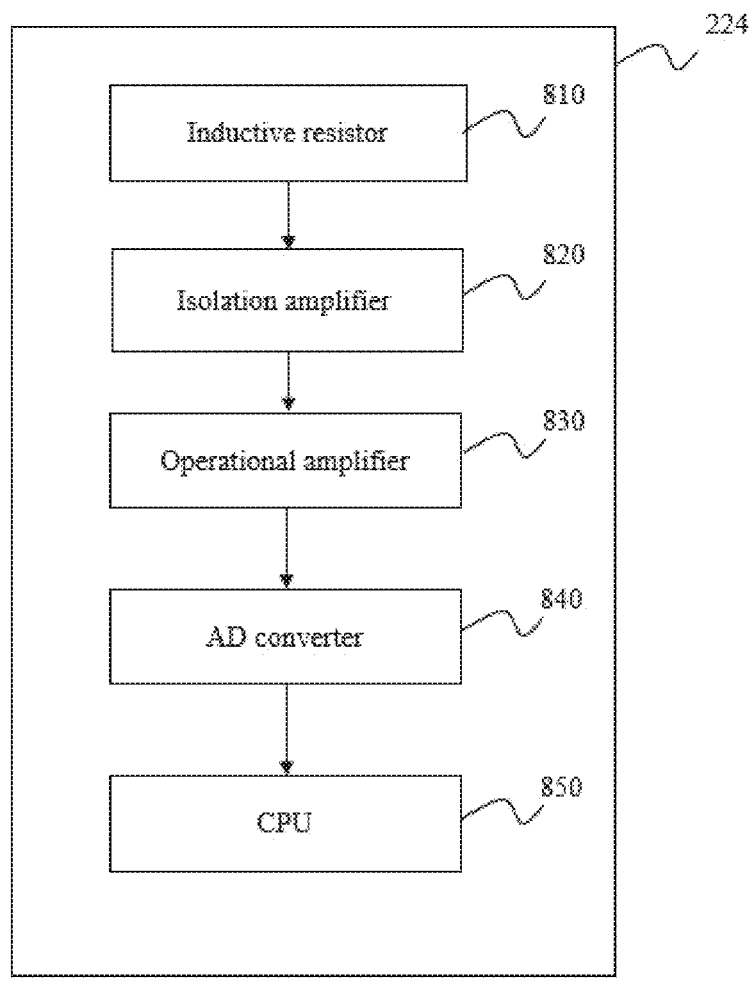
FIG. 8 is a block diagram of the protection module 224 according to some embodiments of the present disclosure.

FIG. 8 is a block diagram of the protection module 224 according to some embodiments of the present disclosure. The protection module 224 may include an inductive resistor 810, an isolation amplifier 820, an operational amplifier 830, an A/D converter 840, and a CPU 850.

The inductive resistor 810 may be connected in series with the motor 550. The protection module 224 may acquire a partial voltage of the inductive resistor 810 through a detecting current of the inductive resistor 810. To allow the motor 550 to have a higher partial voltage, the resistance of the inductive resistor 810 may be less than 2 ohm, such as 1 ohm. In some embodiments, the partial voltage of the inductive resistor 810 may be less than 1 volt. The partial voltage of the inductive resistor 810 may be amplified by the isolation amplifier 820 and/or the operational amplifier 830. The amplified partial voltage of the inductive resistor 810 may be an analogue signal. The analogue signal may be converted to a digital signal by the A/D converter 840. The digital signal may be transmitted to the CPU 850. In some embodiments, the CPU 850 may determine whether the operation of the motor 550 is normal according to the digital signal. As an example, the CPU 850 may determine that the operation of the motor 550 is abnormal when the digital signal exceeds a threshold. The CPU 850 may transmit the result to the control unit 320.

In some embodiments, the CPU 850 may assess the degree of aging of the motor 550. In some embodiments, the CPU 850 may assess the degree of aging of the motor 550 according to working current of the motor 550. In some embodiments, the working current of the motor 550 may be equivalent to the current of the inductive resistor 810. In some embodiments, the working current of the motor 550 may increase as the degree of aging increases, when the motor 550 drives a same load. In some embodiments, the CPU 850 may determine the multiple of a working current and an initial current of the motor 550. The initial current of the motor 550, as used herein, may be the current of the motor 550 obtained at an early period of the motor 550 driving a same load. The early period, as used herein, may be a period that the motor is new and is not used before. In some embodiments, the CPU 850 may further compare the multiple of a working current and an initial current of the motor 550 with a threshold. In some embodiments, the threshold may be determined according to an aging curve of the motor 550. In some embodiments, the threshold may be 1.1, 1.2, etc. The CPU 850 may transmit the comparison result to the control unit 320. The control unit 320 may generate a warning signal according to the comparison result.

It should be noted that the above description is merely provided for the purposes of illustration, and not intended to limit the scope of the present disclosure. For persons having ordinary skills in the art, multiple variations and modifications may be made under the teachings of the present disclosure. For example, the protection module 224 may further include another inductive resistor. As another example, the CPU 850 may be unnecessary and removed from the control unit 320. However, those variations and modifications do not depart from the scope of the present disclosure.

Figure 9:
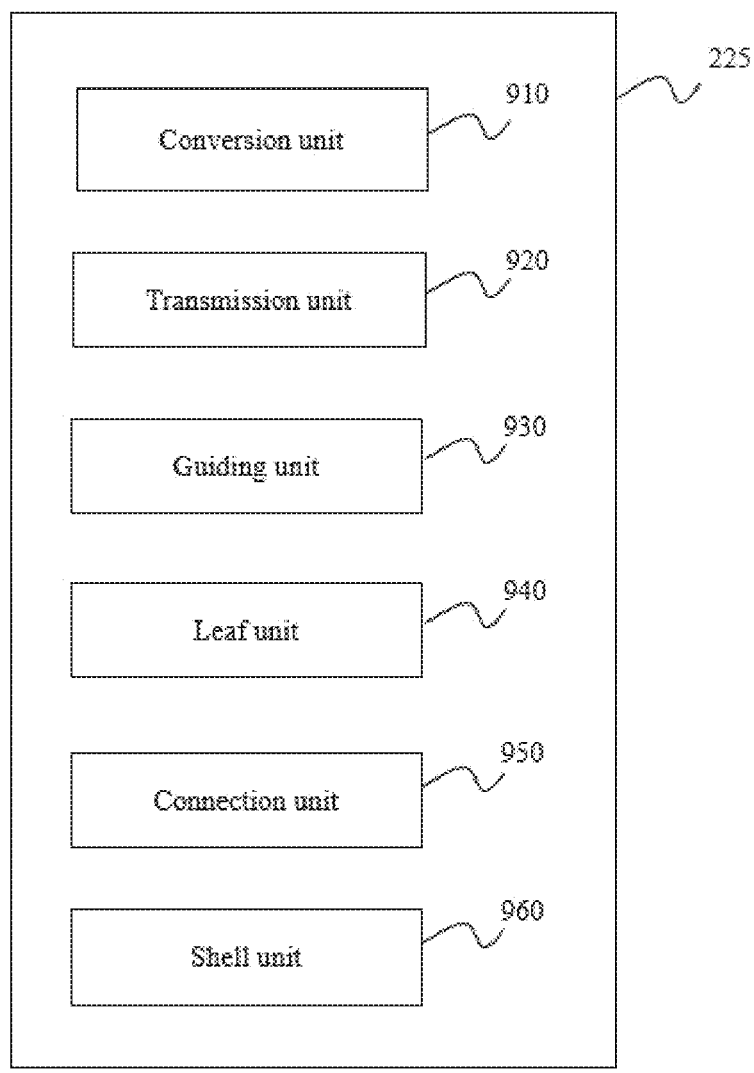
FIG. 9 is a block diagram of the leaf module 225 according to some embodiments of the present disclosure.

FIG. 9 is a block diagram of the leaf module 225 according to some embodiments of the present disclosure. The leaf module 225 may include a conversion unit 910, a transmission unit 920, a guiding unit 930, a leaf unit 940, a connection unit 950, and a shell unit 960.

The conversion unit 910 may convert the movement form of the motor 550. In some embodiments, the conversion unit 910 may convert a rotation motion of the motor 550 to a linear motion. In some embodiments, the conversion unit 910 may be the conversion piece described in connection with FIG. 15. Details regarding the conversion piece may be found elsewhere in the present disclosure. See, for example, the description of FIG. 15. In some embodiments, the conversion unit 910 may convert the direction of the movement of the motor 550, for example, convert a motion in the horizontal direction to a motion in the vertical direction. In some embodiments, the conversion unit 910 may be the conversion piece described in FIG. 24. Details regarding the conversion piece may be found elsewhere in the present disclosure. See, for example, the description of FIG. 24.

In some embodiments, the conversion unit 910 may be connected to the transmission unit 920 directly or indirectly and may drive the transmission unit 920. In some embodiments, the conversion unit 910 may be connected to the transmission unit 920 indirectly through the connection unit 950.

The transmission unit 920 may transmit the movement between different units in the leaf module 225. In some embodiments, the transmission unit 920 may transmit the movement between the conversion unit 910 and the leaf unit 940. In some embodiments, the transmission unit 920 may enlarge the distance, and/or change the relative location between the conversion unit 910 and the leaf unit 940.

In some embodiments, the transmission unit 920 may include a flexible transmission shaft. The transmission shaft may be and incompressible. In some embodiments, the transmission shaft may be made from a non-magnetic material. Merely by way of example, the non-magnetic material may be stainless steel, an alloy (e.g., aluminum ally, etc.), rubber, plastics, or the like, or the combination thereof. In some embodiments, the transmission unit 920 may be the transmission shaft illustrated in FIG. 14 and the description thereof. In some embodiments, the transmission unit 920 may be the transmission shaft illustrated in FIG. 22-B and the description thereof.

In some embodiments, the transmission unit 920 may include a transmission line and an elastic piece. In some embodiments, the transmission line may be a steel wire. In some embodiments, the transmission unit 920 may be the transmission line and the elastic piece illustrated in FIG. 23 and the description thereof. Details regarding the transmission line and the elastic piece may be found elsewhere in the present disclosure. See, for example, the description of FIG. 23.

Figure 20:
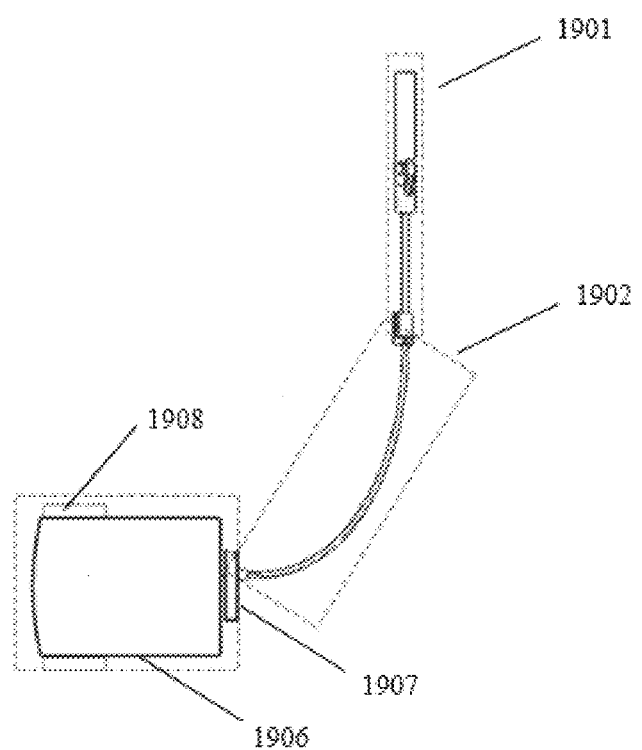
FIG. 20 illustrates an exemplary construction of the grating unit in FIG. 19-A and FIG. 19-B according to some embodiments of the present disclosure.

The guiding unit 930 may control the moving path of the transmission unit. In some embodiments, the guiding unit 930 may be a sleeve having a hollow structure. In some embodiments, the shape of the sleeve may be linear or curved, such as an L shape as shown in FIG. 14-C and FIG. 14-D. In some embodiments, the guiding unit 930 may be a guiding box. In some embodiments, the sleeve may be placed in the guiding box. In some embodiments, the shape of the guiding box may be the same as or similar to the shape of the sleeve. In some embodiments, the shape of the guiding box may be different from the shape of the sleeve. In some embodiments, the shape of the guiding box may be linear or curved, such as an L shape as shown in FIG. 14-A. In some embodiments, the guiding unit 930 may include a sleeve as illustrated in FIG. 14-C and FIG. 14-D and the description thereof. In some embodiments, the guiding unit 930 may include a guiding box as illustrated in FIG. 14-A and FIG. 14-B and the description thereof. In some embodiments, the guiding unit 930 may include a sleeve as illustrated in FIG. 20-A and the description thereof. In some embodiments, the guiding unit 930 may include a guiding wheel and a reeling wheel as illustrated in FIG. 23 and the description thereof.

The leaf unit 940 may form a conformal shaping. In some embodiments, the leaf unit 940 may include a plurality of leaves and a leaf guiding rail. The leaves may move independently in and out of the path of beams (e.g., particle beams, etc.) to provide a conformal shaping. The thickness of the leaves may influence the conformal shaping. In some embodiments, the thickness of a leaf may be from 0.8 mm to 2.2 mm, from 0.8 to 1.6 mm, from 0.8 to 1.3 mm, from 1.0 to 1.8 mm, from 1.0 to 1.5 mm. In some embodiments, a leaf may be made of a high atomic numbered material, for example, tungsten. The leaf guiding rail may limit the moving path of a leaf. In some embodiments, the leaf guiding rail may include a leaf guide groove. A leaf may be placed in the leaf guiding rail. The leaf may undergo a linear motion within the leaf guiding rail. In some embodiments, descriptions of a leaf of the leaf unit 940 may be found elsewhere in the present disclosure. See, for example, FIG. 14, FIG. 20, and FIG. 23, and the description thereof.

Figure 18:
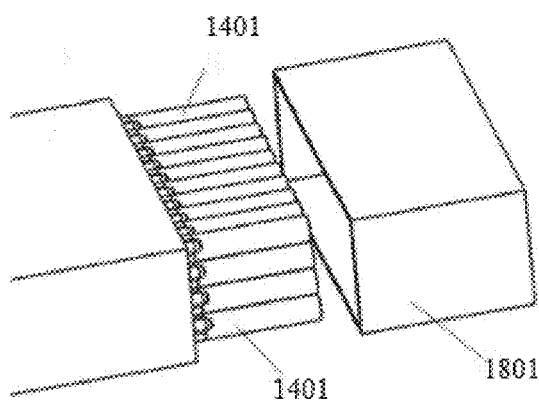
FIG. 18 illustrate an exemplary shell of the MLC 1400 according to some embodiments of the present disclosure.

The connection unit 950 may connect different units in the leaf module 225. In some embodiments, the connection unit 950 may connect the conversion unit 910 and the transmission unit 920. In some embodiments, the connection unit 950 may connect the transmission unit 920 and the guiding unit 930. In some embodiments, the connection unit 950 may connect the guiding unit 930 and the leaf unit 940. In some embodiments, the connection unit 950 may connect the transmission unit 920 and the leaf unit 940. In some embodiments, the connection may be in the form of a removal connection, a non-removal connection, or the like, or a combination thereof. In some embodiments, the connection unit 950 may include a hard straight bar. In some embodiments, the connection unit 950 may include a connection piece as illustrated in FIG. 18 and the description thereof.

The motor 550 may be contained in the shell unit 960. In some embodiments, the shell unit 960 may shield the motor 550 from the magnetic field. In some embodiments, the shell unit 960 may be made from stainless steel, aluminum, or the like, or an alloy thereof.

It should be noted that the above description is merely provided for the purposes of illustration, and not intended to limit the scope of the present disclosure. For persons having ordinary skills in the art, multiple variations and modifications may be made under the teachings of the present disclosure. For example, the conversion unit 910 may be unnecessary and removed. As another example, the leaf module 225 may further have a motor and a support for the motor. However, those variations and modifications do not depart from the scope of the present disclosure.

Figure 10:
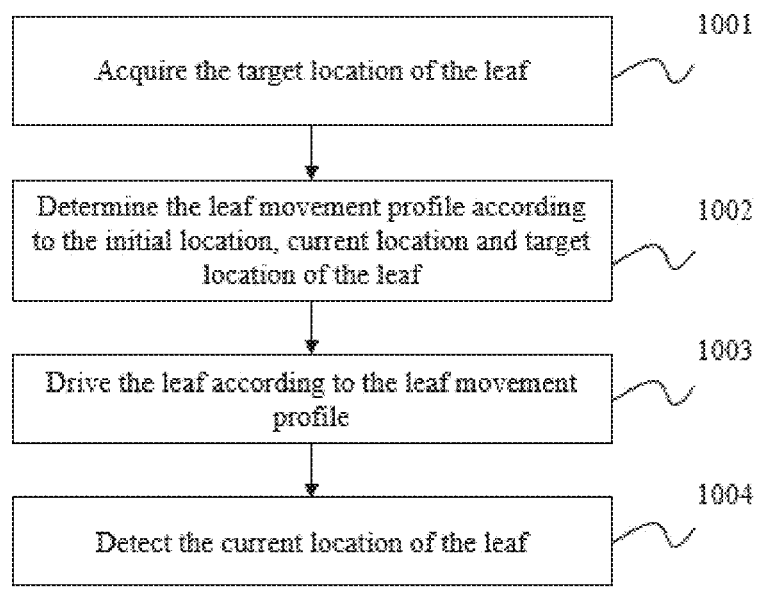
FIG. 10 illustrates an exemplary process 1000 for the collimator system 110 according to some embodiments of the present disclosure.

FIG. 10 illustrates an exemplary process 1000 for the collimator system 110 according to some embodiments of the present disclosure. In step 1001, the target location of the leaf may be acquired. In some embodiments, the target location of the leaf may be acquired through the I/O unit 310. In some embodiments, the target location of the leaf may be provided by a user, from a master computer, etc. The master computer may provide control instructions to the collimator system 110. In some embodiments, the target location of the leaf may be determined based on a treatment region of a subject (e.g., a patient, etc.). In some embodiments, the leaf target location may be set according to a desired conformal shaping.

In step 1002, the leaf movement profile may be determined based on, e.g., the initial location, a current location, the target location of the leaf, the time associated with a location of the leaf, the time available for a leaf to reach its target location, or the like, or a combination thereof. In some embodiments, the leaf movement profile may be determined by the control unit 320. In some embodiments, the leaf movement profile may include three stages, referred to as a first stage, a second stage, and a third stage. In some embodiments, the leaf speed may increase in the first stage, be constant in the second stage, and decrease in the third stage. In some embodiments, the leaf speed may decrease at a constant rate (or slope) or at a variable rate (or slope).

In step 1003, a leaf may be driven according to the leaf movement profile. In some embodiments, the leaf may be driven based on a driving signal generated by the control unit 320. In some embodiments, the step 1003 may be conducted in the driving module 222. In step 1004, the current location of the leaf may be determined based on the leaf initial location and the leaf displacement. In some embodiments, the determination of the current location of the leaf may be performed by the control unit 320. In some embodiments, the current location of the leaf may be used to determine or update the leaf movement profile.

Merely by way of example, an initial movement profile of a leaf, including a first stage, a second stage, and a third stage, may be provided. The third stage of the initial movement profile may be updated in real time or periodically based on the measured leaf current locations and the time available for the leaf to reach its target location. In some embodiments, the first stage and/or the second stage of the movement profile may be updated such that the leaf reaches its target location at a desired time.

It should be noted that the above description is merely provided for the purposes of illustration, and not intended to limit the scope of the present disclosure. For persons having ordinary skills in the art, multiple variations and modifications may be made under the teachings of the present disclosure. For example, the process 1000 may further include determining whether the movement of the leaf is normal. As another example, the process 1000 may further include stopping the movement of the leaf when an abnormality occurs is identified. However, those variations and modifications do not depart from the scope of the present disclosure.

Figure 11:
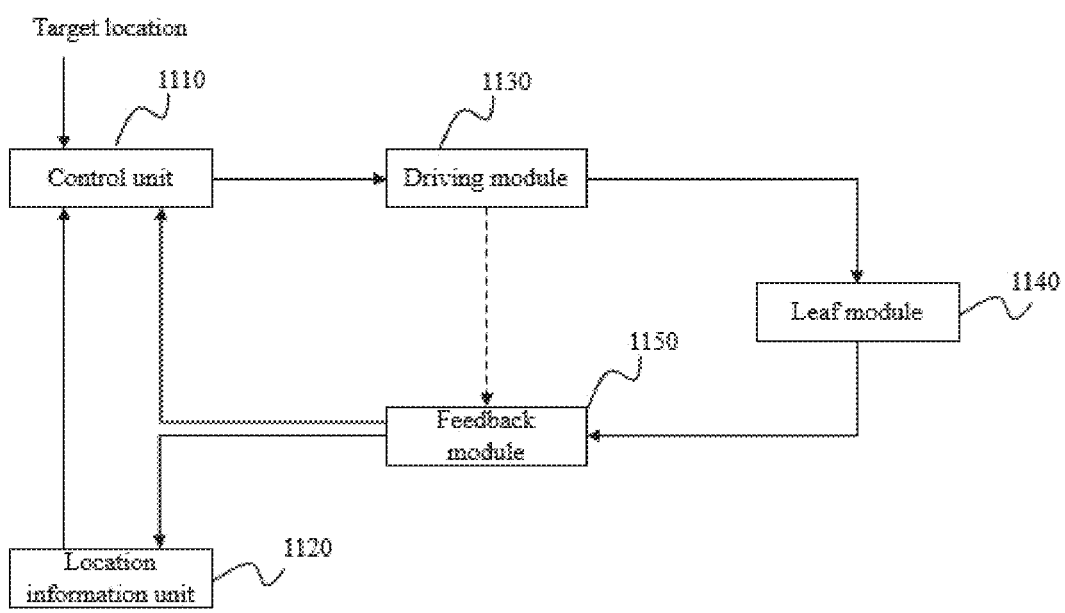
FIG. 11 is an example of the collimator system 110 according to some embodiments of the present disclosure.

FIG. 11 is an example of the collimator system 110 according to some embodiments of the present disclosure. As shown in FIG. 11, the collimator system 1100 may include a control unit 1110, a location information unit 1120, a driving module 1130, a leaf module 1140, and a feedback module 1150.

The control unit 1110 may acquire the leaf target location. The leaf target location may be determined based on a desired conformal shaping. The control unit 1110 may acquire the leaf initial location that may be set as the leaf zero location. The control unit 1110 may determine the leaf current location according to the leaf initial location and the leaf displacement acquired by, for example, the feedback module 1150. The control unit 1110 may acquire the leaf location offset from the location information unit 1120. The leaf location offset may be determined based on the leaf current location and the leaf target location. The leaf location offset may also be determined based on the correction factor $V_t * T_m$ as described in connection with FIG. 3. The control unit 1110 may determine the leaf movement profile based on the leaf initial location, the leaf current location, the leaf target location, the leaf location offset, relevant time information, or the like, or a combination thereof. The control unit 1110 may generate a driving signal. The driving module 1130 may drive, based on the driving signal, the motor in the driving module 1130. The motor may drive the leaf in the leaf module 1140 to move following the movement profile. The leaf may reach the leaf target location and facilitate the formation of the desired conformal shaping.

Figure 12:
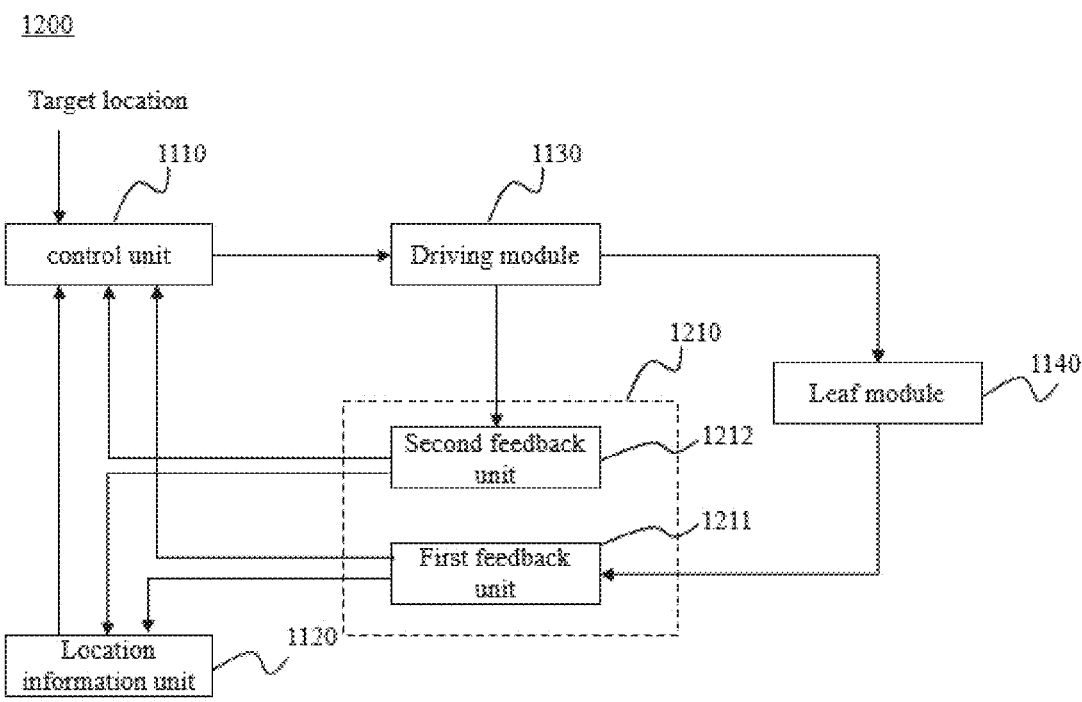
FIG. 12 is an example of the collimator system 110 according to some embodiments of the present disclosure.

FIG. 12 is an example of the collimator system 110 according to some embodiments of the present disclosure. As shown in FIG. 12, the collimator system 1200 may include a control unit 1110, a location information unit 1120, a driving module 1130, a leaf module 1140, and a feedback module 1210. The feedback module 1210 may include a first feedback unit 1211 and a second feedback unit 1212.

The first feedback unit 1211 may detect the movement of the leaf in the leaf module 1140. The first feedback unit 1211 may determine the leaf displacement according to the movement of the leaf in the leaf module 1140. The second feedback unit 1212 may detect the motion of the motor in the driving module 1130. The second feedback unit 1212 may determine the leaf displacement based on the motion of the motor.

In some embodiments, the leaf displacement determined by the first feedback unit 1211 and the second feedback unit 1212 may be equivalent. The control unit 1110 may determine the leaf movement profile as illustrated in FIG. 11 and the description thereof. "Equivalent," as used herein, may indicate that the leaf displacement determined by the first feedback unit 1211 and the leaf displacement determined by the second feedback unit 1212 are exactly the same, or that the difference between the leaf displacement determined by the first feedback unit 1211 and the leaf displacement determined by the second feedback unit 1212 is less than a threshold. See, for example, FIG. 7 and the description thereof.

In some embodiments, the leaf displacement determined by the first feedback unit 1211 and the leaf displacement determined by the second feedback unit 1212 may be inequivalent. The control unit 1110 may generate a driving signal. The driving signal may be transmitted to the driving module 1130. The driving signal may include a stop signal. The stop signal may stop the motor in the driving module 1130 such that the leaf in the leaf module 1140 may stop.

Figure 13:
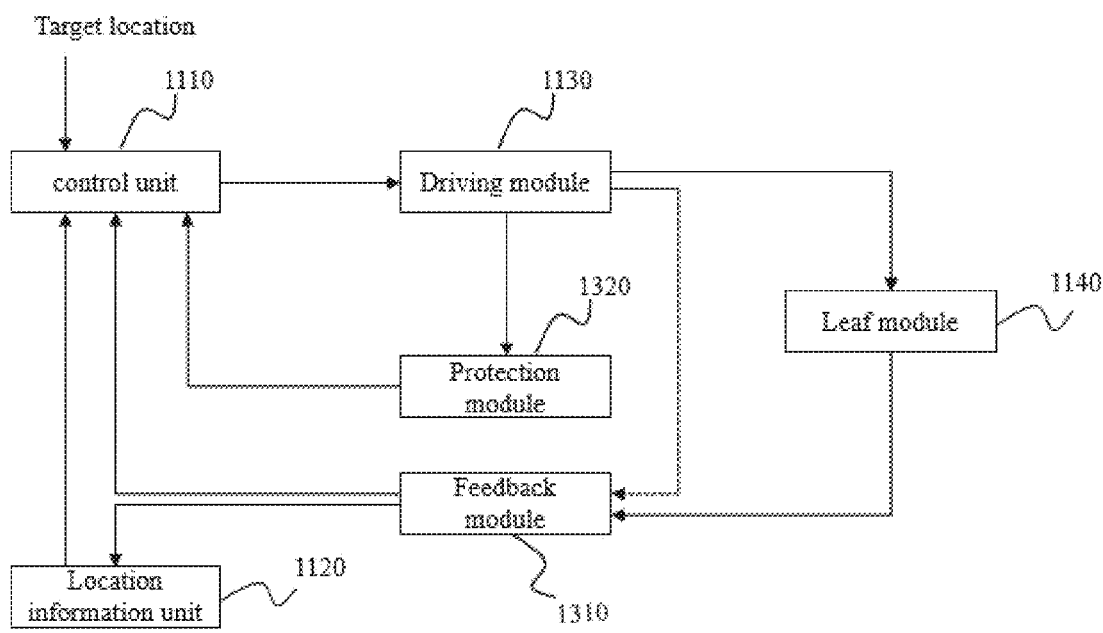
FIG. 13 is an example of the collimator system 110 according to some embodiments of the present disclosure.

FIG. 13 is an example of the collimator system 110 according to some embodiments of the present disclosure. As shown in FIG. 13, the collimator system 1300 may include a control unit 1110, a location information unit 1120, a driving module 1130, a leaf module 1140, a feedback module 1310, and a protection module 1320.

In some embodiments, the feedback module 1310 maybe a feedback module 1150 as illustrated in FIG. 11 and the description thereof. In some embodiments, the feedback module 1310 may include a first feedback unit and a second feedback unit, similar to the feedback module 1210 illustrated in FIG. 12 and the description thereof.

The protection module 1320 may detect the current of the motor in the driving module 1130. In some embodiments, the protection module 1320 may determine whether the operation of the motor in the driving module 1130 is normal based on the detected current of the motor. In some embodiments, if the detected current of the motor exceeds a threshold, the operation of the motor may be deemed abnormal. See, for example, FIG. 8 and the description thereof. In some embodiments, the protection module 1320 may assess the degree of aging of the motor in the driving module 1130. The assessment may be based on the detected current of the motor. The protection module 1320 may assess the difference of the working current and the initial current of the motor, and determine the degree of aging of the motor according to an aging curve of the motor. See, for example, FIG. 8 and the description thereof.

When the operation of the motor is abnormal, the control unit 1110 may generate driving signal and transmit the driving signal to the driving module. The driving signal may be stop signal. The stop signal may stop the motor and the leaf in the leaf module 1140 may stop. When the degree of aging is more than a threshold, the control unit 1110 may generate warning signal and transmit the warning signal to operators to take actions. The actions may include changing the motor in the driving module 1130.

FIG. 14-A to FIG. 14-D illustrate an exemplary MLC according to some embodiments of the present disclosure. FIG. 14-A illustrates the front view of the MLC. FIG. 14-B illustrates the top view of the MLC. FIG. 14-C and FIG. 14-D illustrate an internal structure of the MLC. As shown in FIG. 14-A to FIG. 14-D, the MLC 1400 may include a motor 1401, a guiding box 1402, a connection piece 1403, a leaf guiding rail 1404, a leaf 1405, a conversion piece 1406, a transmission shaft 1407, and a sleeve 1408. The motor 1401 may be placed on a supporting base (for example, 1601 in FIG. 16). The sleeve 1408 may be located within the guiding box 1402. The leaf guiding rail 1404 may include a leaf guiding groove. The leaf guiding groove may limit the moving path of the leaf 1405. The transmission shaft 1407 may connect the motor 1401 and the leaf 1405. The transmission shaft 1407 may be flexible. The transmission shaft 1407 may be incompressible. The transmission shaft 1407 may include a hollow structure. The sleeve 1408 may include a hollow structure. The guiding box 1402, the transmission shaft 1407, or the sleeve 1408 may have an L-shape. Description regarding the connection piece 1403 may be found elsewhere in the present disclosure. See, for example, FIG. 17 and the description thereof. The thickness of the leaf 1405 may influence the conformal shaping of radiation beams. The thickness of the leaf 1405 may be from 0.8 mm to 2.2 mm, from 0.8 mm to 1.6 mm, from 0.8 mm to 1.3 mm, from 1.0 mm to 1.8 mm, from 1.0 mm to 1.5 mm, etc. The leaf 1405 may be made from a material that has properties including, for example, high density, high hardness, proper machinability, or the like, or a combination thereof. The leaf 1405 may be made of, for example, tungsten, aluminum, magnesium, stainless steel, copper, or the like, or an alloy thereof.

The motor 1401 may be operationally connected to the conversion piece 1406. The conversion piece 1406 may be operationally connected to the transmission shaft 1407. The transmission shaft 1407 may be operationally connected to the leaf 1405 via the connection piece 1403. The transmission shaft 1407 may be placed in the hollow structure of the sleeve 1408. The sleeve 1408 may be placed in the guiding box 1402 in a distributed form. The leaf 1405 may be placed in the leaf guiding rail 1404.

For the purposes of illustration, the motor 1401 may undergo a clockwise rotation. Via the conversion of the conversion piece 1406, the transmission shaft 1407 may undergo a linear movement toward to the motor 1401. Details regarding the conversion piece 1406 may be found elsewhere in the present disclosure. See, for example, FIG. 15 and FIG. 16 and the description thereof. The connection piece 1403 and the leaf 1405 may undergo a linear movement driven by the transmission shaft 1407. The leaf 1405 may retract to the guiding box 1402 along the leaf guiding rail 1404 in the form of a linear movement. The motor 1401 may undergo an anticlockwise rotation. Via the conversion of the conversion piece 1406, the transmission shaft 1407 may undergo a linear movement away from the motor 1401. The connection piece 1403 and the leaf 1405 may undergo a linear movement driven by the transmission shaft 1407. The leaf 1405 may stretch out of the guiding box along the leaf guiding rail 1404 in the form of a linear movement.

Figure 15:
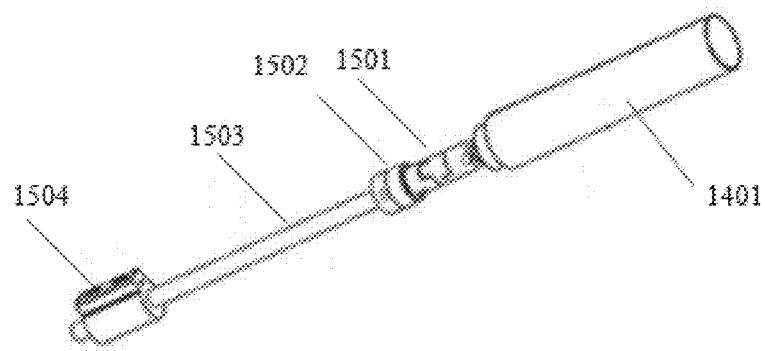
FIG. 15 illustrate an exemplary structure of the conversion piece 1406 according to some embodiments of the present disclosure.

FIG. 15 illustrate an exemplary structure of the conversion piece 1406 according to some embodiments of the present disclosure. The conversion piece 1406 may include a three-stage coupling 1501, a bearing 1502, a screw 1503, and a nut 1504. The nut 1504 may be placed around the screw 1503. The nut 1504 may match the threads of the screw 1503. The nut 1504 may be fixedly connected to the transmission shaft 1407. The three-stage coupling 1501 may include a first coupling, a second coupling, and a third coupling. The first coupling, the second coupling, and the third coupling may be arranged in a coaxial direction along the axis of the three-stage coupling 1501. The first coupling may include a first cavity. The third coupling may include a second cavity. The output shaft of the motor 1401 may be connected to the screw 1503 through the three-stage coupling 1501 and the bearing 1502. The output shaft of the motor 1401 may be placed in the first cavity. One end of the screw 1503 may be placed in the second cavity. The other end of the screw 1503 may be placed in the hollow structure of the transmission shaft 1407. The length of the hollow structure in the transmission shaft 1407 may be equal to or less than the length of the transmission shaft 1407. The aperture of the hollow structure in the transmission shaft 1407 may be greater than the aperture of the screw 1503.

When the motor 1401 is operating, the rotational motion of the output shaft of the motor 1401 may be output to the end of the screw 1503 in the second cavity of the third coupling through the second coupling. Due to the three-stage coupling, the disalignment of the motor 1401 output shaft and the screw 1503 may be compensated. The screw 1503 may undergo a rotational movement. The nut 1504 may undergo a linear movement along the screw 1503. During the linear movement of the nut 1504, the screw 1503 may undergo a movement in the hollow structure of the transmission shaft 1407. The hollow structure in the transmission shaft 1407 may be located at the end of the transmission shaft 1407 where the end of the transmission shaft 1407 is connected to the nut 1504. The hollow structure may provide room for the movement of the screw 1503. The transmission shaft 1407 connected fixedly with the nut 1504 may undergo a linear movement. Details regarding the conversion piece 1406 may be found elsewhere in the present disclosure. See, for example, FIG. 16 and the description thereof.

Figure 16:
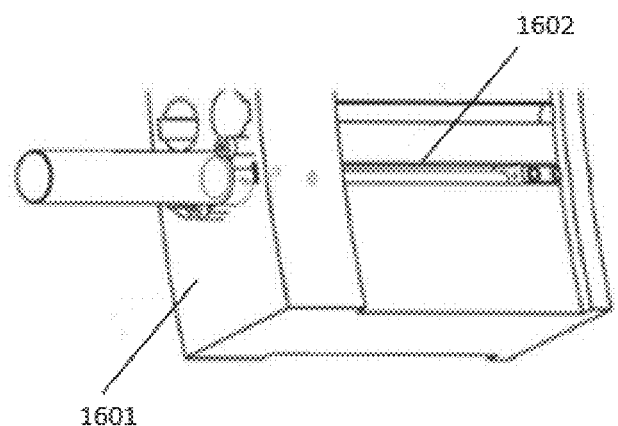
FIG. 16 illustrates an exemplary inner structure of the supporting base 1601 according to some embodiments of the present disclosure.

FIG. 16 illustrates an exemplary inner structure of the supporting base 1601 according to some embodiments of the present disclosure. The supporting base 1601 may include a nut guiding rail 1602. The nut guiding rail 1602 may limit the moving path of the nut 1504. When the motor 1401 is operating, the screw 1503 may undergo a rotational movement. Due to the limitation of the nut guiding rail 1602, the nut 1504 may undergo a linear movement along the screw 1503. Due to the fixed connection between the nut 1504 and the transmission shaft 1407, the transmission shaft 1407 may undergo a linear movement. The rotational motion of the motor 1401 may be converted to a linear movement of the transmission shaft 1407.

FIG. 17-A to FIG. 17-C illustrate exemplary connections between the leaf 1405 and the transmission shaft 1407 according to some embodiments of the present disclosure. FIG. 17-A and FIG. 17-B illustrate clamp connections between the leaf 1405 and the transmission shaft 1407. FIG. 17-C illustrates a bolted connection between the leaf 1405 and the transmission shaft 1407. As shown in FIG. 17-A and FIG. 17-B, one end of the connection piece 1403 may include an expansion bump 1701. The leaf 1405 may include a groove 1702. The expansion bump 1701 may have a shape of a hemicycle, a trapezoid, etc. The expansion bump 1701 may match the groove 1702. The transmission shaft 1407 may be operationally connected to the leaf 1405 via the expansion bump 1701 and the groove 1702. As shown in FIG. 17-C, one end of the connection piece 1403 may include a bending part. The bending part may have an L-shape. Two bolts 1703 may be placed on the back side of the leaf 1405. The back side of the leaf, as used herein, may be the right side of the leaf 1405 along the horizontal movement of the leaf 1405. The bending part of the connection piece 1403 may be connected to the leaf 1405.

FIG. 18 illustrate an exemplary shell of the MLC 1400 according to some embodiments of the present disclosure. As shown in the figure, the motor 1401 may be placed on the supporting base. The shell 1801 may be a hollow cuboid and may cover the motor 1401. The shell 1801 may shield the motor 1401 from a magnetic field. In some embodiments, the shell 1801 may be made from stainless steel, aluminum, or the like, or an alloy thereof.

FIG. 19-A to FIG. 19-B illustrate an exemplary MLC according to some embodiments of the present disclosure. FIG. 19-A illustrates the top view of the MLC. FIG. 19-B illustrates a sectional view of the MLC. As shown in FIG. 19-A and FIG. 19-B, the MLC 1900 may include a driving piece 1901, a transmission piece 1902, a supporting base 1903, a brace 1904, a mounting plate 1905, a guiding box 1906, a first connection piece 1907, and a leaf 1908. The driving piece 1901, the transmission piece 1902, and the leaf 1908 may form a grating unit. The driving piece 1901 may include a motor and a conversion piece. The motor and the transmission piece 1902 may be connected through the conversion piece. The conversion piece may convert a rotational movement of the motor to a linear movement of the transmission piece 1902. Details regarding the conversion piece may be found elsewhere in the present disclosure. See, for example, FIG. 15 and FIG. 16 and the description thereof.

The transmission piece 1902 may include a transmission shaft 2107 (shown in FIG. 21-A) and a sleeve 2101 (shown in FIG. 21-A). The transmission shaft 2107 and the sleeve 2101 may be flexible. The sleeve 2101 may bend with different bending radius. The bending radius may be determined based on relative location of magnetic field and the motor and diameter of the transmission shaft 2107. The diameter of the transmission shaft 2107 may be, for example, from 0.5 mm to 1.0 mm. Deformation of the sleeve 2101 and friction between the transmission shaft 2107 and the sleeve 2101 may increase as the bending radius decreases. Gear lubricant may be placed in the sleeve 2101 to reduce the friction between the transmission shaft 2107 and the sleeve 2101. The gear lubricant may be radiation resistant. The relative location of the motor in the driving piece 1901 from the leaf 1908 may be adjusted by adjusting the bending radius. By adjusting the relative location, the interference between the magnetic field and the motor in the driving piece 1901 may be reduced when the leaf 1908 is subject to the magnetic field. The sleeve 2101 may include an extension spring. The transmission shaft 2107 may move independently in the sleeve 2101. The transmission shaft 2107 and the sleeve 2101 may be made from a non-magnetic material including, for example, stainless steel, an alloy (e.g., aluminum ally, etc.), rubber, plastics, or the like, or a combination thereof.

The leaf 1908 may be made from a material that has properties including, for example, high density, high hardness, proper machinability, or the like, or a combination thereof. The leaf 1908 may be made of, for example, tungsten, aluminum, magnesium, stainless steel, copper, or the like, or an alloy thereof. Thickness of the leaf 1908 may influence the conformal shaping of radiation beams. The thickness of the leaf 1405 may be from 0.8 mm to 2.2 mm, from 0.8 mm to 1.6 mm, from 0.8 mm to 1.3 mm, from 1.0 mm to 1.8 mm, from 1.0 mm to 1.5 mm, etc.

As shown in the figures, the leaf 1908 may be divided into two groups. The two groups may be placed on the opposite sides of the mounting plate 1905. At least a part of the driving piece 1901 may be located on the supporting base 1903. The supporting base 1903 may be held by one end of the brace 1904. The other end of the brace 1904 may be placed on the mounting plate 1905. A guiding box 1906 may be attached to the mounting plate 1905. The leaf 1908 may be placed in the guiding box 1906. The guiding box 1906 may include a leaf guiding groove (not shown in the figures). The leaf guiding groove may be congruous with the leaf 1908 and limit the moving path of the leaf 1908. The leaf 1908 may undergo a reciprocal movement in the leaf guiding groove. The MLC 1900 may form a desired conformal shaping according to the shape of a target region (e.g., a treatment region, etc.) through the reciprocal movement of the leaf 1908.

The MLC 1900 may further include a second connection piece (not shown in the figure). The second connection piece may be operationally connect the transmission shaft 2107 and the leaf 1908. The second connection piece may be the connection piece 1403 as illustrated in FIG. 17-A to FIG. 17-C and the description thereof.

The MLC 1900 may further include a shell (not shown in the figure). The shell may cover the motor in the driving piece 1901 and shield the motor from a magnetic field. The shell may be made from stainless steel, aluminum, or the like, or an alloy thereof. The shell 1801 illustrated in FIG. 18 may be used.

FIG. 20 illustrates an exemplary construction of the grating unit in FIG. 19-A and FIG. 19-B according to some embodiments of the present disclosure. The driving piece 1901 may be connected to the transmission piece 1902. Details regarding connection between the transmission piece 1902 and the driving piece 1901 may be found elsewhere in the present disclosure. See, for example, FIG. 21-A and the description thereof. The driving piece 1901 and the leaf 1908 may be connected through the first connection piece 1907. Details regarding connection between the transmission piece 1902 and the leaf 1908 may be found elsewhere in the present disclosure. See, for example, FIG. 21-B and the description thereof. The leaf 1908 may be placed in the guiding box 1906.

When the motor in the driving piece 1901 is operating, the rotating motion from the output shaft of the motor may be output to the conversion piece in the driving piece 1901. The conversion piece in the driving piece 1901 may convert the rotational motion from the motor to the linear movement of the transmission shaft 2107 in the transmission piece 1902. The conversion piece in the driving piece 1901 may be the conversion piece 1406 in MLC 1400. Details regarding the conversion piece in the driving piece 1901 may be found elsewhere in the present disclosure. See, for example, FIG. 15 and FIG. 16 and the description thereof. The transmission shaft 2107 may undergo a linear movement toward to the motor or away from the motor. Correspondingly, the leaf 1908 may retract to or stretch out of the guiding box 1906. By the movement of the leaf 1908, a desired conformal shape may be obtained.

FIG. 21-A and FIG. 21-B illustrate an exemplary immobilization regarding the sleeve 2101 according to some embodiments of the present disclosure. FIG. 21-A illustrates the connection between the sleeve 2101 and the supporting base 1903. FIG. 21-B illustrates the connection between the sleeve 2101 and the leaf guiding box 1906.

As shown in FIG. 21-A, the sleeve 2101 may be fixed on the supporting base 1903 through a sleeve fixed piece 2102 and a nut 2106. The sleeve fixed piece 2102 may have an opening 2108. An outside diameter of the opening 2108 may match the diameter of the sleeve 2101. The nut 2106 may have an opening 2109. The outside diameter of the opening 2109 may match the diameter of the transmission shaft 2107. One end of the sleeve 2101 may be fixed on the supporting base 1903 through the sleeve fixed piece 2102. The sleeve 2101 may be placed into the opening 2108 and the sleeve 2101 may be fixed by inserting a set screw 2103. One or more set screws 2103 may be used. One end of the transmission shaft 2107 may stretch out of the sleeve 2101 and placed into the opening 2109. The transmission shaft 2107 may be fixed by inserting a set screw 2104. In order to fix the transmission shaft 2107 more stably, the transmission shaft compressing piece 2105 may be inserted into the nut 2106 through an interference fit. The transmission shaft compressing piece 2105 may be configured with an opening (not shown in the figure) of which outside diameter may match the diameter of the transmission shaft 2107. With the transmission shaft 2107 passing through the opening 2109 and the opening of the transmission shaft compressing piece 2105, the transmission shaft 2107 may be fixed by the set screw 2104. One or more set screw 2104 may be used.

As shown in FIG. 21-B, the sleeve 2101 may be fixed on the guiding box 1906 through the first connection piece 1907. The first connection piece 1907 may be placed behind the leaf 1908. The first connection piece 1907 may be connected to the guiding box 1906. The first connection piece 1907 may have an opening 2110. The outside diameter of the opening 2110 may match the diameter of the sleeve 2101. The opening 2110 may be a threaded opening. The transmission shaft 2107 may be screwed into the threaded opening to form a fixed connection. The opening 2110 may be configured along the horizontal movement of the leaf 1908. The deformation of the transmission shaft 2107 may be reduced during the movement of the leaf 1908. In order to make the connection between the sleeve 2101 and the first connection 1907 more stably, a fastener structure (not shown in the figure) may be included in the first connection piece 1907.

The sleeve 2101, the transmission shaft 2107, and the transmission shaft compressing piece 2105 may be made from a non-magnetic material. The sleeve 2101 and the transmission shaft compressing piece 2105 may be made from stainless steel, copper, or the like, or an alloy thereof. The transmission shaft 2107 may be made from a non-magnetic material with high hardness, for example, stainless steel, etc. The nut 2106 may be made from, for example, a radiation resistant resin composite.

FIG. 22-A to FIG. 22-C illustrate an exemplary MLC according to some embodiments of the present disclosure. FIG. 22-A illustrates the configuration of the MLC 2200. As shown in FIG. 22-A, the MLC may include a driving unit 2201 and a leaf unit 2202. The leaf unit 2202 may be driven by the driving unit 2201. The leaf unit 2202 may facilitate the formation of a desired conformal shape of radiation beams according to a target region (e.g., a treatment region, etc.). The leaf unit 2202 may be connected to the driving unit 2201 by a transmission piece (not shown in the figure). Details regarding the transmission piece may be found elsewhere in the present disclosure. See, for example, FIG. 23 and the description thereof. The driving unit 2201 and the leaf unit 2202 may be spaced from each other. There may be more installation space for the driving unit 2201 without the limitation of the leaf unit 2202.

FIG. 22-B illustrates an exemplary construction of the driving unit 2201 in MLC 2200. The driving unit 2201 may include a motor supporting base 2203, a plurality of motors 2204, and a motor brace 2205. The motor 2204 may provide a driving force to the leaf unit 2202. The motor 2204 may be placed on the motor supporting base 2203. The motor brace 2205 may be placed on the motor supporting base 2203. The motor 2204 may be fixed by the motor brace 2205. The motor supporting base 2203 and the motor brace 2205 may be integrated into one piece, or two independent pieces connected using a connection piece. The motors 2204 may be placed in one or more layers. The motors 2204 may be placed toward a single direction or different directions (e.g., opposite directions, etc.). For instance, the layer arrangement for the motors 2204 may be determined based on the spatial configuration of a device that may be used with the MLC 2200. As shown in FIG. 22-B, the motors 2204 may be placed in an upper layer and a lower layer arranged in multiple rows. The motors 2204 in an upper layer and the motors 2204 in a lower layer below the upper layer may be toward opposite directions. The diameter of the motor 2204 may be, for example, 10 mm.

FIG. 22-C illustrates an exemplary configuration of the leaf unit 2202. As shown in FIG. 22-C, the leaf unit 2202 may include a guiding box 2206 and at a leaf 2207. The guiding box 2206 may be configured with a leaf guiding groove (not shown in the figure). The leaf guiding groove may hold and guide the leaves 2207. A leaf 2207 may be placed into a corresponding leaf guiding groove. The leaf 2207 may undergo a reciprocal movement in the leaf guiding groove. The MLC 2200 may provide a desired conformal shaping of radiation beams based on the shape of a target region through the movements of the leaves 2207. A leaf 2207 may be made from a material that has properties including, for example, high density, high hardness, proper machinability, or the like, or a combination thereof. The leaf 2207 may be made of, for example, tungsten, aluminum, magnesium, stainless steel, copper, or the like, or an alloy thereof. The thickness of the leaf 2207 may influence the conformal shaping of radiation beams. The thickness of the leaf 2207 may be from 0.8 mm to 2.2 mm, from 0.8 mm to 1.6 mm, from 0.8 mm to 1.3 mm, from 1.0 mm to 1.8 mm, from 1.0 mm to 1.5 mm, etc.

FIG. 23-A to FIG. 23-D illustrate an exemplary configuration of MLC 2200 according to some embodiments of the present disclosure. FIG. 23-A and FIG. 23-B illustrate MLC 2200 with the leaf 2207 retracting to the guiding box 2206. FIG. 23-C and FIG. 23-D illustrate MLC 2200 with the leaf 2207 extending out of the guiding box 2206. As shown in FIG. 23-A, the MLC 2200 may further include a worm 2301, a gear 2302, a transmission line 2303, a first guiding wheel 2304, a spring 2305, a supporting base 2306, and a guiding bar 2307. The worm 2301 and the gear 2302 may change the direction of the rotational motion output by the motor 2204. Details regarding to the worm 2301 and the gear 2302 may be found elsewhere in the present disclosure. See, for example, FIG. 24 and the description thereof. The transmission line 2303 may transmit movement from the motor 2204 to a leaf 2207, and/or provide a pulling force to the leaf 2207. The transmission line 2303 may be made from a non-magnetic material. For instance, the transmission line may include a steel wire. The first guiding wheel 2304 may guide the transmission line 2303. The spring 2305 may be in a compressed state. The spring 2305 may provide an elastic force to the leaf 2207. The guiding bar 2307 may hold and/or guide the spring 2305. The spring 2305 and the guiding bar 2307 may be made from a non-magnetic material including, for example, stainless steel, copper, or the like, or an alloy thereof. The MLC 2200 may further include a shell (not shown in the figure). The shell may cover the motor 2204 and shield the motor 2204 from a magnetic field. The shell may be made from a non-magnetic material including, for example, stainless steel, aluminum, or the like, or an alloy thereof. The shell may be the shell 1801 as illustrated in FIG. 18 and the description thereof.

The motor 2204 may be connected to the transmission line 2303 with the worm 2301 and the gear 2302. The transmission line 2303 may be connected to the leaf 2207 through the first guiding wheel 2304. Details regarding connection between the transmission line 2303 and the leaf 2207 may be found elsewhere in the present disclosure. See, for example, FIG. 25 and the description thereof. The first guiding wheel 2304 may be placed on the supporting base 2306. One end of the guiding bar 2307 may be fixed on the supporting base 2306. The other end of the guiding bar 2307 may be connected to the leaf 2207. The end of the guiding bar 2307 connected with the supporting base 2306 may bend, which may reduce the length of the MLC 2200 along the horizontal movement of the leaf 2207. One end of the spring 2305 may be fixed on the supporting base 2306. The other end of the spring 2305 may be connected to the leaf 2207. Details regarding connection between the spring 2305 and the leaf 2207 may be found elsewhere in the present disclosure. See, for example, FIG. 25 and the description thereof. The spring 2305 may be placed around the guiding bar 2307. The spring 2305 may deform along the guiding bar 2307.

An output end of the motor 2204 may be connected with the worm 2301. The worm 2301 may mesh with the gear 2302 and drive the gear 2302. When the motor 2204 is operating, the worm 2301 may undergo a rotational motion in a direction, then the gear 2302 may undergo a rotational motion in a different direction. The transmission line 2303 may pass through the first guiding wheel 2304, and be connected to the leaf 2207. For the purposes of illustration, the length of the transmission line 2303 may be shorter when the motor 2204 undergoes clockwise rotation; the length of the transmission line 2303 may be longer when the motor 2204 undergoes an anticlockwise rotation.

When the motor 2204 undergoes a clockwise rotation, the length of the transmission line 2303 may be shorter. The transmission line 2303 may provide the pulling force to the leaf 2207. The leaf 2207 may retract to the guiding box 2206. When the motor 2204 undergoes an anticlockwise rotation, the length of the transmission line 2303 may be longer. The spring 2305 in a compressed state may provide an elastic force to the leaf 2207 such that the leaf 2207 may stretch out of the guiding box 2206. The elastic force provided by the spring 2305 may be greater than the gravity that the leaf 2207 is subject to. By this way, the transmission line 2303 and the spring 2305 in concert may control the movement of the leaf 2207. An angle between the elastic force provided by the spring 2305 and the pulling force provided by the transmission line 2303 may be 175-185 degrees.

FIG. 24 illustrate details regarding the configuration of the MLC 2200 according to some embodiments of the present disclosure. As shown in FIG. 24, the motor brace 2205 may include a gear brace 2401 and a reeling wheel 2402. The gear 2302 may be fixed on the motor brace 2205 by the gear brace 2401. The reeling wheel 2402 and the gear 2302 may be arranged coaxially and undergo a rotational motion coaxially. When the speed of the motor 2204 is constant, the speed of the gear 2302 may be constant. When the speed of the reeling wheel 2402 may be constant, the speed of the leaf 2207 may increase with the diameter of the reeling wheel 2402. The speed of the leaf 2207 may increase by increasing the diameter of the reeling wheel 2402. The transmission line 2303 may be wrapped around the reeling wheel 2402. The reeling wheel 2402 may include an encoder (not shown in the figures). The encoder may detect the displacement of the leaf 2207. The reeling wheel 2402 and the encoder may be arranged coaxially and undergo a rotational motion coaxially. The number of rounds of the encoder detected by the encoder may be equal to the number of rounds of the reeling wheel 2402. The circumference of the reeling wheel 2402 may be measured. The displacement of the leaf 2207 may be determined by multiplying the circumference of the reeling wheel 2402 by the number of rounds of the reeling wheel 2402.

The MLC 2200 may further include a second guiding wheel 2404. The second guiding wheel 2404 may guide the transmission line 2303. The second guiding wheel 2404 may be fixed on the motor brace 2205 by a guiding wheel brace 2403. The transmission line 2303 may be connected to the leaf 2207 with stretching out of the reeling wheel 2402 and passing through the second guiding wheel 2404. The second guiding wheel 2404 may include an encoder 2405. The encoder 2405 may detect the displacement of the leaf 2207. The second guiding wheel 2404 and the encoder 2405 may be arranged coaxially and undergo a rotational motion coaxially. The number of rounds of the encoder 2405 detected by the encoder 2405 may be equal to number of rounds of the second guiding wheel 2404. The circumference of the second guiding wheel 2404 may be measured. The displacement of the leaf 2207 may be determined by multiplying the circumference of the second guiding wheel 2404 by the number of rounds of the second guiding wheel 2404.

When the motor 2204 is operating, the worm 2301 may rotate in a direction. Due to the mesh between the worm 2301 and the gear 2302, the gear 2302 may rotate in a direction different from the rotation direction of the worm 2301. For instance, the gear 2302 may rotate in a direction perpendicular to the rotation direction of the worm 2301. When the motor 2204 stops operating, the spring 2305 in a compressed state may provide an elastic force to the leaf 2207. The leaf 2207 may provide a pulling force to the reeling wheel 2402. The gear 2302 may undergo a rotational movement with the rotating reeling wheel 2402. The leaf 2207 may undergo linear movement. In order to prevent the leaf 2207 from moving when the motor 2204 stops operating, the worm 2301 and the gear 2302 may be self-locking. Self-locking, as used herein, may be that the gear 2302 may undergo a rotational motion when the worm 2301 undergoes a rotational motion; the worm 2301 may not undergo a rotational motion when the gear 2302 undergoes a rotational motion. Due to the self-lock between the worm 2301 and the gear 2302, the worm 2301 may not rotate and the leaf 2207 may stop moving when the motor 2204 stops operating.

The transmission line 2303 may wrap around the reeling wheel 2402, and pass through the first guiding wheel 2304 and the second guiding wheel 2404, connecting the reeling wheel 2402 and the leaf 2207. By changing the locations and/or the orientations of the first guiding wheel 2304 and/or the second guiding wheel 2404, the location of a motor 2204 may be changed. By changing the location of a motor 2204, the relative location of the motor 2204 and the leaf 2207 may be changed. When the MLC 2200 is used in a magnetic field, the motor 2204 may be placed away from the magnetic field, and the influence between the motor 2204 and the magnetic field may be reduced. The motors 2204 may be placed such that the distances between different motors 2204 may be different. By this way, there may be more installation space for encoders used to detect displacement of the leaves 2207 in the driving unit 2201.

FIG. 25-A and FIG. 25-B illustrate an exemplary configuration of the leaves 2207 according to some embodiments of the present disclosure. FIG. 25-A illustrates the front side of the leaves 2207. The back side of a leaf 2207, as used herein, may be the left side of the leaf 2207 along the horizontal movement of the leaf 2207. FIG. 25-B illustrates the back side of the leaves 2207.

As shown in FIG. 25-B, a leaf 2207 may include a leaf tail 2501. The leaves 2207 may be located in one or more rows. The leaf tail 2501 may operationally connect the transmission line 2303 and the leaf 2207. The leaf tail 2501 may operationally connect the spring 2305 and the leaf 2207. The leaf tail 2501 may include a sliding groove. The guiding bar 2307 may enter or exit the sliding groove when the leaf 2207 is moving, so that the leaf 2207 moves relatively to the guiding bar 2307. The sliding groove may be located on the guiding bar 2307. The leaf tail 2501 may include a structure congruous with the sliding groove.

In order to avoid collision of the spring 2305 and the guiding bar 2307, the leaf tails 2501 may be located at different locations on the neighboring leaves.

Having thus described the basic concepts, it may be rather apparent to those skilled in the art after reading this detailed disclosure that the foregoing detailed disclosure is intended to be presented by way for example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "block," "module," "apparatus," "unit," "component," "device," or "system". Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution—e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities of ingredients, properties such as molecular weight, reaction conditions, and so forth, used to describe and claim certain embodiments of the application are to be understood as being modified in some instances by the term "about," "approximate," or "substantially". For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A multi-leaf collimator drive system, the multi-leaf collimator comprising a plurality of leaves and a plurality of motors configured to drive the plurality of leaves, the system comprising:
    a control module configured to program a movement profile of each leaf of the plurality of leaves according to parameters, for each leaf of the plurality of leaves, the parameters including at least one of leaf location information of the leaf, a time associated with the leaf location information of the leaf, a leaf location offset of the leaf, a distance that the leaf travels to reach the leaf target location, or a distance travelled by the leaf, wherein the leaf location information of the leaf includes at least one of an initial location of the leaf, a current location of the leaf, or a target location of the leaf;
    a driving module configured to drive the plurality of motors of the collimator to move the plurality of leaves according to the programed movement profile; and
    a position feedback module configured to provide the current locations of the leaves as a feedback to the control module;
    wherein, for each leaf of said plurality of leaves, the control module programs the movement profile of the leaf according to a pattern having a first stage, a second stage, and a third stage, according to the movement profile, the leaf moving from the initial location to the target location, and wherein the stages of the movement profile are updated based on the leaf current location and the time available for the leaf to reach its target location.

2. A collimator system comprising the drive system of claim 1, further comprising:

a plurality of elongated flexible transmission units, each of the plurality of leaves being operably connected to one of the plurality of motors through one of the plurality of transmission units, wherein each of the plurality of transmission units includes a transmission line and an elastic piece operably connected to the transmission line, and the transmission line provides one leaf of the plurality of leaves a first force, and the elastic piece provides the leaf a second force.

3. The collimator system of claim 2, wherein
the first force includes a pulling force to the leaf; and
the second force is an elastic force to the leaf.

4. The system of claim 1, wherein for each of the plurality of leaves, the speed of the leaf movement decreases at a constant rate in the third stage.

5. The system of claim 1, wherein for each of the plurality of leaves, the control module controls the speed of the leaf movement to dynamically decrease the speed of the leaf movement at a variable rate in the third stage.

6. The system of claim 5, wherein for each of the plurality of leaves, the variable rate is determined based on a distance that the leaf moves in the third stage.

7. The system of claim 1, wherein for each of the plurality of leaves, the third stage occupies 10% to 30% of a time period of the movement of the leaf from the initial location to the leaf target location.

8. The system of claim 1, wherein for each of the plurality of leaves, a leaf location offset is determined based on a current location of the leaf and the target location of the leaf.

9. The system of claim 1, wherein for each leaf of the plurality of leaves, the position feedback module comprises a displacement transducer sensing the displacement of the leaf or an encoder installed on a motor of the plurality of motors.

10. The system of claim 1, wherein for each leaf of the plurality of leaves, the position feedback module comprises a first position feedback module corresponding to the leaf, a second position feedback module corresponding to a motor of the plurality of motors, and the control module is configured to assess whether the movement of the leaf is normal by determining if the position feedback of the leaf by the first position feedback module and the position feedback of the leaf by the second position feedback module fulfills a predetermined relationship.

11. The system of claim 10, wherein the first position feedback module comprises a displacement transducer sensing the displacement of the leaf and the second position feedback module comprises an encoder or a potentiometer installed on the motor.

12. The collimator system of claim 2, further comprising a protection module, wherein for each of the plurality of motors, the protection module is configured to monitor a working condition of the motor.

13. The collimator system of claim 12, wherein the protection module includes at least one of an inductive resistor, an isolation amplifier, an operational amplifier, an A/D converter, or a central processing unit (CPU).

14. The system of claim 1, wherein in the first stage, a speed of the leaf movement increases, in the second stage, the speed of the leaf movement is constant, and in the third stage, the speed of the leaf movement decreases.

15. A method for driving the leaves of a multi-leaf collimator using a multi-leaf collimator driving system, the collimator comprising a plurality of leaves and a plurality of motors configured to drive the plurality of leaves and the collimator driving system comprising a control module, a driving module, and a position feedback module; the method comprising:
for each of the plurality of leaves:
using the control module to receive a predetermined target location of the leaf;
using the control module to:
program a movement profile of the leaf based on parameters including at least one of leaf location information of the leaf, a time associated with the leaf location information of the leaf, a leaf location offset of the leaf, a distance that the leaf travels to reach the leaf target location, or a distance travelled by the leaf, wherein the leaf location information of the leaf includes at least one of an initial location of the leaf, a current location of the leaf, or a target location of the leaf, the leaf movement profile comprising a first stage, a second stage, and a third stage, according to the movement profile, the leaf moving from the initial location to the target location;
using the driving module to move the leaf according to the leaf movement profile; and
using the control module to detect the current location of the leaf;
wherein the stages of the movement profile are updated based on the current locations of each leaf and the time available for the leaf to reach its target location.

16. The method of claim 15, further comprising, for each leaf of the plurality of leaves:
increasing the speed of the leaf movement during the first stage, keeping the speed of the leaf movement constant during the second stage, and decreasing the speed of the leaf movement during the third stage.

17. The method of claim 15, the collimator further comprising:
a plurality of transmission units, each of the plurality of leaves being operably connected to one of the plurality of motors through one of the plurality of transmission units, wherein each of the plurality of transmission units includes a transmission line and an elastic piece operably connected to the transmission line, and the transmission line provides one leaf of the plurality of leaves a first force, and the elastic piece provides the leaf a second force, and
the method further comprising using the driving module to move the leaf according to the leaf movement profile by controlling the transmission unit and the motor.

18. The method of claim 15, further comprising:
determining a first leaf displacement of the leaf;
determining a second leaf displacement of the leaf; and
assessing whether the movement of the leaf is normal based on the first leaf displacement and the second leaf displacement.

19. The method of claim 18, wherein the assessing whether the movement of the leaf is normal based on the first leaf displacement and the second leaf displacement includes:
if a difference between the first leaf displacement and the second leaf displacement is less than a threshold, determining that the movement of the leaf is normal; or
if a difference between the first leaf displacement and the second leaf displacement is greater than or equal to a threshold, determining that the movement of the leaf is abnormal.

20. The method of claim 17, wherein
the first force includes a pulling force to the leaf; and
the second force is an elastic force to the leaf.

\* \* \* \* \*